US011229428B2

(12) United States Patent
Jackson

(10) Patent No.: US 11,229,428 B2
(45) Date of Patent: Jan. 25, 2022

(54) SELF-LOCKING TISSUE CINCHING SUTURE SYSTEM

(71) Applicant: Jeffrey David Jackson, Salt Lake City, UT (US)

(72) Inventor: Jeffrey David Jackson, Salt Lake City, UT (US)

(*) Notice: Subject to any disclaimer, the term of this patent is extended or adjusted under 35 U.S.C. 154(b) by 336 days.

(21) Appl. No.: 16/060,366

(22) PCT Filed: Mar. 7, 2017

(86) PCT No.: PCT/US2017/021101
§ 371 (c)(1),
(2) Date: Jun. 7, 2018

(87) PCT Pub. No.: WO2017/189096
PCT Pub. Date: Nov. 2, 2017

(65) Prior Publication Data
US 2019/0038276 A1 Feb. 7, 2019

Related U.S. Application Data

(60) Provisional application No. 62/329,086, filed on Apr. 28, 2016, provisional application No. 62/327,796, filed on Apr. 26, 2016.

(51) Int. Cl.
*A61B 17/04* (2006.01)
*A61B 17/06* (2006.01)
*A61F 2/08* (2006.01)

(52) U.S. Cl.
CPC .... *A61B 17/0401* (2013.01); *A61B 17/06128* (2013.01); *A61F 2/0811* (2013.01);
(Continued)

(58) Field of Classification Search
CPC .......... A61B 17/0401; A61B 17/06119; A61B 7/06128; A61B 2017/0409;
(Continued)

(56) References Cited

U.S. PATENT DOCUMENTS 3,570,497 A 3/1971 Lemole
8,231,654 B2 7/2012 Kaiser et al.
(Continued)

FOREIGN PATENT DOCUMENTS

EP 2 548 519 A2 1/2013
EP 2 572 650 A1 3/2013
(Continued)

OTHER PUBLICATIONS

International Preliminary Report on Patentability dated Oct. 30, 2018 in International Patent Application No. PCT/US2017/021101.
(Continued)

*Primary Examiner* — Jocelin C Tanner
(74) *Attorney, Agent, or Firm* — Maschoff Brennan; Jonathan M. Benns

(57) ABSTRACT

A suture implant can include one or more suture cords having: a splice; a first free end extending from a first end of the at least one splice; an adjustable first loop extending from a second end of the at least one splice; a second free end extending from a first end of the at least one splice; a needled second loop having a cord portion extending from the first end of the at least one splice; a needle on the needled second loop; and an adjustable third loop extending from a second end of the at least one splice that has the second free end extending from the first end, wherein the second free end is connected to the adjustable third loop, wherein the adjustable first loop and adjustable third loop are interconnected and looped around each other.

17 Claims, 26 Drawing Sheets

(52) U.S. Cl.
CPC ............... *A61B 2017/0404* (2013.01); *A61B 2017/0409* (2013.01); *A61B 2017/0414* (2013.01); *A61B 2017/0464* (2013.01); *A61B 2017/06185* (2013.01); *A61F 2002/0823* (2013.01); *A61F 2002/0852* (2013.01)

(58) Field of Classification Search
CPC .. A61B 2017/0464; A61B 2017/06185; A61B 2017/0404; A61B 2017/0414; A61F 2/0811; A61F 2002/0823; A61F 2002/0852
See application file for complete search history.

(56) References Cited

U.S. PATENT DOCUMENTS

| | | | |
|---|---|---|---|
| 8,231,674 | B2 | 7/2012 | Albertorio et al. |
| 8,663,324 | B2 | 3/2014 | Schmieding et al. |
| 8,936,621 | B2 | 1/2015 | Denham et al. |
| 9,168,124 | B2 | 10/2015 | Guerra et al. |
| 9,642,610 | B2 | 5/2017 | Albertorio et al. |
| 10,076,407 | B2 | 9/2018 | Albertorio et al. |
| 10,448,945 | B2 | 10/2019 | Bachmaier et al. |
| 10,517,587 | B2 | 12/2019 | Denham et al. |
| 10,716,557 | B2 | 7/2020 | Denham et al. |
| 10,864,028 | B2 | 12/2020 | Zajac et al. |
| 2005/0033363 | A1* | 2/2005 | Bojarski .......... A61B 17/06166 606/228 |
| 2008/0082128 | A1 | 4/2008 | Stone |
| 2008/0188935 | A1* | 8/2008 | Saylor ................. A61F 2/0811 623/13.14 |
| 2008/0208252 | A1* | 8/2008 | Holmes ............... A61B 17/842 606/232 |
| 2010/0256677 | A1* | 10/2010 | Albertorio ........... A61F 2/0811 606/232 |
| 2010/0268273 | A1* | 10/2010 | Albertorio ......... A61B 17/0401 606/232 |
| 2011/0098727 | A1* | 4/2011 | Kaiser ............... A61B 17/0401 606/144 |
| 2011/0208240 | A1* | 8/2011 | Stone ............... A61B 17/06166 606/232 |
| 2012/0046693 | A1* | 2/2012 | Denham .............. A61B 17/842 606/232 |
| 2013/0096612 | A1* | 4/2013 | Zajac ................ A61B 17/0469 606/232 |
| 2014/0276992 | A1 | 9/2014 | Stone et al. |
| 2014/0277448 | A1 | 9/2014 | Guerra et al. |
| 2015/0066081 | A1 | 3/2015 | Martin |
| 2015/0201929 | A1 | 7/2015 | Dooney, Jr. et al. |
| 2016/0007989 | A1 | 1/2016 | Overes et al. |
| 2018/0193015 | A1 | 7/2018 | Denham et al. |

FOREIGN PATENT DOCUMENTS

| | | |
|---|---|---|
| EP | 2 581 047 A1 | 4/2013 |
| EP | 2 676 612 A2 | 12/2013 |
| EP | 2238944 B1 | 10/2015 |
| EP | 2777613 B1 | 6/2017 |
| EP | 3 228 279 A1 | 10/2017 |

OTHER PUBLICATIONS

International Search Report and Written Opinion dated Jul. 17, 2017 in International App. No. PCT/US17/21101.
U.S. Appl. No. 13/102,182, filed Mar. 6, 2011; Equivalent to U.S. Pat. No. 8,231,654, cited herewith.
U.S. Appl. No. 11/541,506, filed Sep. 29, 2006; Equivalent to U.S. App. Publication No. 2008/0082128, cited herewith.
U.S. Appl. No. 62/180,347, filed Jun. 16, 2015.
U.S. Appl. No. 62/200,458, filed Aug. 3, 2015.
U.S. Appl. No. 62/212,307, filed Aug. 31, 2015.
U.S. Appl. No. 62/253,457, filed Nov. 10, 2015.

* cited by examiner

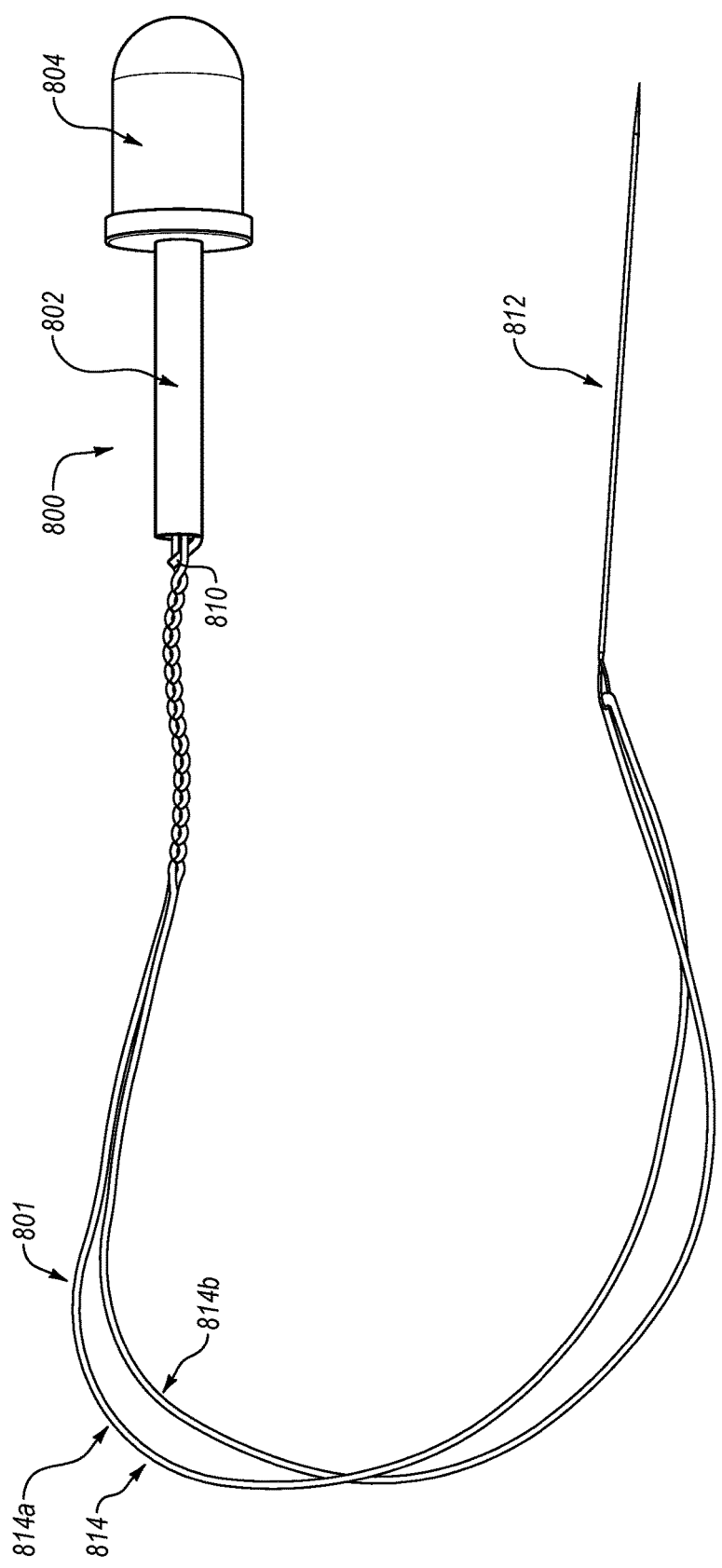
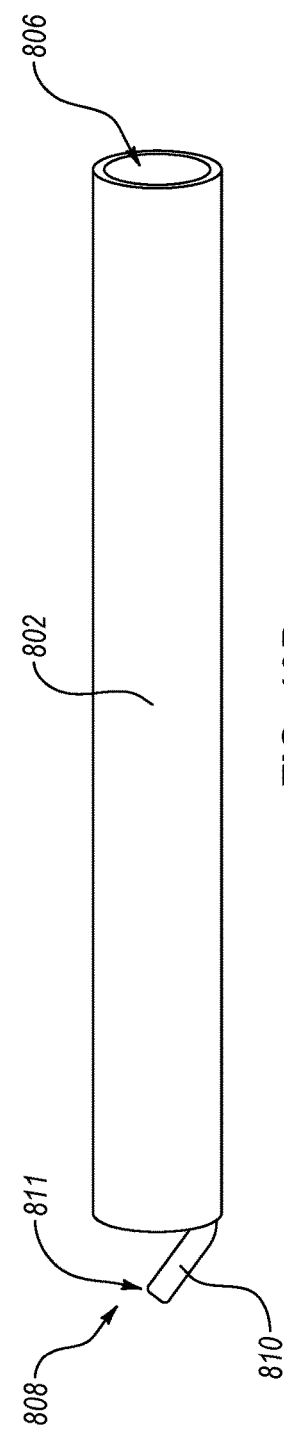
FIG. 10A
FIG. 10B

SELF-LOCKING TISSUE CINCHING SUTURE SYSTEM

CROSS-REFERENCE

This patent application is a section 371 nationalization of PCT Application No. PCT/US2017/021101 filed Mar. 7, 2017, which PCT Application claims priority to U.S. Provisional Application Nos. 62/327,796 filed Apr. 26, 2016 and 62/329,086 filed Apr. 28, 2016, which PCT and provisional applications are incorporated herein by specific reference in its entirety.

BACKGROUND

It has been found that traditional sutures and use thereof to cinch two different tissues together can injure one or both tissues and complicate the surgical procedure. The suture can unfavorably include the cord passing through one of the tissues in a manner where the cord slides against the tissue, such as sliding against a wall of a hole in the tissue, and acts as a saw to slice through the tissue or otherwise tear the tissue. The sliding action of the cord can abrade the tissue and wear or otherwise tear down the structure of the tissue, which can cause the hole to increase in size and take on an injury from the cut of the sliding cord. In some instances, pulling tension onto a tissue that has the suture cord sliding against the tissue can tear the tissue and pull the suture cord from the injured tissue.

SUMMARY

In one embodiment, a suture implant comprising one or more suture cords having: at least one splice; a first free end extending from a first end of the at least one splice; an adjustable first loop extending from a second end of the at least one splice that has the first free end extending from the first end, wherein the first free end is connected to the adjustable first loop; a second free end extending from a first end of the at least one splice; a needled second loop having a cord portion extending from the first end of the at least one splice that has the first free end extending therefrom and extending from the first end of the at least one splice that has the second free end extending therefrom; a needle on the needled second loop; and an adjustable third loop extending from a second end of the at least one splice that has the second free end extending from the first end, wherein the second free end is connected to the adjustable third loop, wherein the adjustable first loop and adjustable third loop are interconnected and looped around each other. In one aspect, the first free end is extending from the first end of a first splice of the at least one splice; and the second free end is extending from the first end of the first splice of the at least one splice. In one aspect, the first free end is extending from the first end of a first splice of the at least one splice; and the second free end is extending from the first end of a second splice of the at least one splice, wherein the first splice is separate from the second splice. In one aspect, the first free end is extending from the first end of a first splice of the at least one splice; and the second free end is extending from the first end of a second splice of the at least one splice, wherein the first splice is connected to the second splice. In one aspect, the first free end is extending from the first end of a first splice of the at least one splice; and the second free end is extending from the first end of a second splice of the at least one splice, wherein the first splice and the second splice are splice portions of a common splice. In one aspect, the at least one splice is a single splice. In one aspect, the at least one splice is two separate splices. In one aspect, the one or more suture cords is a single suture cord. In one aspect, the one or more suture cords is two separate suture cords that are coupled together.

In one embodiment, the suture implant includes a knot on the needled second loop proximal to the first end of the at least one splice. In one aspect, the knot is on the needled second loop and the first end of the at least one splice. In one aspect, the knot is at an end of the first free end. In one aspect, the knot is at an end of the second free end.

In one embodiment, the suture implant includes a member having at least one aperture therethrough, and at least one of the adjustable first loop or adjustable third loop passes through the at least one aperture so that at least one of the adjustable first loop or adjustable third loop is slidably coupled with the member. In one aspect, the member has a first aperture and second aperture therethrough, and the adjustable first loop passes through the first aperture and the adjustable third loop passes through the second aperture, so that both the adjustable first loop and adjustable third loop are slidably coupled with the member. In one aspect, a member having a first aperture and second aperture therethrough, and a first cord of the adjustable first loop passing through the first aperture and second aperture, and a second cord of the adjustable third loop passing through the first aperture and second aperture oppositely of the first cord, so that both the adjustable first loop and adjustable third loop are slidably coupled with the member. In one aspect, the member is selected from a button, anchor, implant, needle, suture, screw, plate, bone anchor, orthopedic device, or combination thereof.

In one embodiment, the first free end is extending from the first end of a first splice; the adjustable first loop is extending from a second end of the first splice, wherein the first free end is connected to the adjustable first loop; the second free end is extending from the first end of the first splice; the needled second loop is extending from the first end of the first splice; and the adjustable third loop is extending from the second end of the first splice, wherein the second free end is connected to the adjustable third loop, wherein the adjustable first loop and adjustable third loop are interconnected and looped around each other. In one aspect, the one or more suture cords is a single suture cord. In one aspect, the one or more suture cords has the knot associated with the needled second loop so that it is not adjustable. In one aspect, the suture implant includes a member having at least one aperture therethrough, and at least one of the adjustable first loop or adjustable third loop passing through the at least one aperture so that at least one of the adjustable first loop or adjustable third loop is slidably coupled with the member. In one aspect, the suture implant includes a member having a first aperture and second aperture therethrough, and the adjustable first loop passing through the first aperture and adjustable third loop passing through the second aperture, so that both the adjustable first loop and adjustable third loop are slidably coupled with the member. In one aspect, the suture implant includes a member having a first aperture and second aperture therethrough, and a first cord of the adjustable first loop passing through the first aperture and second aperture, and a second cord of the adjustable third loop passing through the first aperture and second aperture oppositely of the first cord, so that both the adjustable first loop and adjustable third loop are slidably coupled with the member. In one aspect, the member is selected from a button, anchor, implant, needle, suture, screw, plate, bone anchor, orthopedic device, or combination thereof.

In one embodiment, the suture implant can include: the first free end extending from the first end of a first splice; the adjustable first loop extending from a second end of the first splice, wherein the first free end is connected to the adjustable first loop; the second free end extending from the first end of a second splice; the needled second loop having a cord portion extending from the first end of the first splice and first end of the second splice; and the adjustable third loop extending from the second end of the second splice, wherein the second free end is connected to the adjustable third loop, wherein the adjustable first loop and adjustable third loop are interconnected and looped around each other. In one aspect, the one or more suture cords is a single suture cord. In one aspect, either free end can include a knot at the end. In one aspect, the suture implant can include a member having at least one aperture therethrough, and at least one of the adjustable first loop or adjustable third loop passing through the at least one aperture so that at least one of the adjustable first loop or adjustable third loop is slidably coupled with the member. In one aspect, the suture implant can include a member having a first aperture and second aperture therethrough, and the adjustable first loop passing through the first aperture and adjustable third loop passing through the second aperture, so that both the adjustable first loop and adjustable third loop are slidably coupled with the member. In one aspect, the suture implant can include a member having a first aperture and second aperture therethrough, and a first cord of the adjustable first loop passing through the first aperture and second aperture, and a second cord of the adjustable third loop passing through the first aperture and second aperture oppositely of the first cord, so that both the adjustable first loop and adjustable third loop are slidably coupled with the member. In one aspect, the member is selected from a button, anchor, implant, needle, suture, screw, plate, bone anchor, orthopedic device, or combination thereof.

In one embodiment, the suture implant can include a knot on the cord portion of the needled second loop that forms a smaller needled second loop extending from the knot. In one aspect, the suture implant can include a knot on the cord portion of the needled second loop that forms a smaller needled second loop extending from the knot, a second suture cord coupled to the knot to provide an enlarged knot. In one aspect, the second suture cord is a rebar stitch in the knot. In one aspect, the suture implant can include a woven portion on the cord portion of the needled second loop that forms a smaller needled second loop extending from the knot.

In one embodiment, the suture implant can include the first free end passing into the first end of the second splice and out from the second end of the second splice; and the second free end passing into the first end of the first splice and out from the second end of the first splice.

In one embodiment, the suture implant can include the first free end passing from the second end of the second splice through an aperture of a member; and the second free end passing from the second end of the first splice through the aperture of the member.

In one embodiment, the suture implant can include the first free end passing through a first aperture of the member; and the second free end passing through a second aperture of the member. This allows the free ends to be pulled through the member during cinching. In one aspect, the member is selected from a button, anchor, implant, needle, suture, screw, plate, bone anchor, orthopedic device, or combination thereof.

In one embodiment, the suture implant can include a suture protector comprising: a tube having a top open end and a bottom open end and lumen therebetween; an elongate divider coupled at one end to the top open end, the elongate divider being flexible so as to extend across the top open end; and a cap having a cap opening and internal chamber, the cap opening receiving the bottom open end of the tube therethrough. In one aspect, the adjustable first loop and adjustable third loop are located within the internal chamber of the cap; a portion of the one or more suture cords extending through the lumen of the tube; and the needled second loop having the needle extending from the top open end, wherein the elongate divider splits the needled second loop by extending through the needled second loop. In one aspect, at least a portion of the adjustable first loop and adjustable third loop are located within the internal chamber of the cap; a portion of the one or more suture cords extending through the lumen of the tube; and the needled second loop having the needle extending from the top open end, wherein the elongate divider is positioned so that a first cord portion extending from the first end of the first splice is on one side of the elongate divider and a second cord portion extending from the first end of the second splice is on the other side of the elongate divider.

In one embodiment, a suture implant system can include a suture protector comprising: a tube having a top open end and a bottom open end and lumen therebetween; and a cap having a cap opening and internal chamber, the cap opening receiving the bottom open end of the tube therethrough; and a suture implant having a portion retained in the internal chamber of the cap, a portion extending through the lumen of the tube, and a portion extending from the top open end of the tube, the suture implant comprising a suture cord having a needle extending from the top open end of the tube. In one aspect, the suture protector can include an elongate divider coupled at one end to the top open end, the elongate divider being flexible so as to extend across the top open end.

In one embodiment, a method of forming the suture implant of one of the embodiments can include: providing a single suture cord; forming a splice and the adjustable first loop by passing the first free end into, through, and out from a lumen of the suture cord so that the splice is formed with a splice second end receiving the first free end therein and the first free end extending out from a splice first end; optionally, passing the second free end through a needle eyelet of a needle; passing the second free end into the splice first end, through the splice and out from the splice second end so as to form the needled second loop extending from the splice first end; and passing the second free end through the adjustable first loop, into the splice second end, through the splice, and out from the splice first end so as to form an adjustable third loop that is interconnected with the adjustable first loop. In one aspect, the method includes passing the adjustable first loop through a first aperture of a member; and passing the second free end through a second aperture of the member, then passing the second free end through the adjustable first loop, then passing the second free end back through the second aperture of the member. In one aspect, the method includes passing the first free end through a first aperture of a member, then passing the first free end through a second aperture of the member, and then passing the first free end through the suture cord to form the splice; and passing the second free end through a second aperture of the member, then passing the second free end through the adjustable first loop, then passing the second free end back through the second aperture of the member.

In one embodiment, a method of forming the suture implant of one of the embodiments includes: providing a single suture cord; forming the first splice and the adjustable first loop by passing the first free end into, through, and out from a lumen of the suture cord so that the first splice is formed with a splice second end receiving the first free end therein and the first free end extending out from a splice first end of the first splice; passing the second free end through a needle eyelet of a needle; and forming the second splice and the adjustable third loop by passing the second free end through the adjustable first loop, then passing the second free end into, through, and out from a lumen of the suture cord so that the second splice is formed with a splice second end receiving the second free end therein and the second free end extending out from a splice first end of the second splice. In one aspect, the method includes passing the adjustable first loop through a first aperture of a member; and passing the second free end through a second aperture of the member, then passing the second free end through the adjustable first loop, then passing the second free end back through the second aperture of the member. In one aspect, the method includes: passing the first free end through a first aperture of a member, then passing the first free end through a second aperture of the member, and then passing the first free end through the suture cord to form the splice; and passing the second free end through a second aperture of the member, then passing the second free end through the adjustable first loop, then passing the second free end back through the second aperture of the member. In one aspect, the method includes forming a knot on the suture cord between the splice first end of the first splice and splice first end of the second splice so that the needled second loop is formed with a needled second loop cord extending from the knot, through the needle eyelet, and back to the knot. In one aspect, the method includes: forming a knot on the suture cord between the splice first end of the first splice and splice first end of the second splice so that the needled second loop is formed with a needled second loop cord extending from the knot, through the needle eyelet, and back to the knot; and stitching a second suture cord to the knot to form an enlarged knot structure.

In one embodiment, the method includes forming a weave portion on the suture cord between the splice first end of the first splice and splice first end of the second splice so that the needled second loop is formed with a needled second loop cord extending from the weave portion, through the needle eyelet, and back to the weave portion. In one aspect, the method includes: cutting the suture cord portion between the splice first end of the first splice and splice first end of the second splice to form a first cord portion extending from the splice first end of the first splice and form a second cord portion extending from the splice first end of the second splice, wherein the suture cord portion may include the needle or may be devoid of the needle; weaving the first cord portion with the second cord portion; placing a needle eyelet of a needle on one of the first cord portion or second cord portion; and joining the first cord portion and second cord portion to form the needled second loop. In one aspect, the joining is by tying a knot with the first cord portion and second cord portion.

In one embodiment, a method of forming the suture implant of one of the embodiments includes: providing a first suture cord having a first free end and third free end; forming the first splice and the adjustable first loop by passing the first free end into, through, and out from a lumen of the first suture cord so that the first splice is formed with a splice second end receiving the first free end therein and the first free end extending out from a splice first end of the first splice, the third free end extending from the splice first end of the first splice; providing a second suture cord having a second free end and fourth free end; forming the second splice and the adjustable third loop by passing the second free end through the adjustable first loop, then passing the second free end into, through, and out from a lumen of the second suture cord so that the second splice is formed with a splice second end receiving the second free end therein and the second free end extending out from a splice first end of the second splice, the fourth free end extending from the splice first end of the second splice; and joining the third free end with the fourth free end so as to form the needled third loop having the needle thereon. In one aspect, the method includes: passing the adjustable first loop through a first aperture of a member; and passing the second free end through a second aperture of the member, then passing the second free end through the adjustable first loop, and then passing the second free end back through the second aperture of the member. In one aspect, the method includes: passing the first free end through a first aperture of a member, then passing the first free end through a second aperture of the member, and then passing the first free end through the first suture cord to form the first splice; and passing the second free end through a second aperture of the member, then passing the second free end through the adjustable first loop, then passing the second free end back through the second aperture of the member, and then passing the second free end through the second suture cord to form the second splice.

In one embodiment, the method includes weaving the first suture cord with the second suture cord by weaving the third free end with the fourth free end; placing a needle eyelet of a needle on one of the third free end or fourth free end; and joining the first suture cord with the second suture cord by joining the third free end or fourth free end to form the needled second loop. In one aspect, the joining is by tying a knot with the third free end and fourth free end.

In one embodiment, a method of cinching a first tissue to a second tissue includes: providing a suture implant in accordance with one of the embodiments; multi-stitching the suture implant to the first tissue; removing the needle from the suture implant; attaching the suture implant to the second tissue; and cinching the first tissue and second tissue together, where during the cinching the suture implant does not slide through or against the first tissue. In one aspect, the cinching includes: pulling the first free end to cinch the adjustable first loop; and pulling the second free end to cinch the adjustable third loop. In one aspect, the first free end and second free end are pulled simultaneously. In one aspect, the first free end and second free end are pulled alternatingly.

In one embodiment, the suture implant includes a knot, enlarged knot, or woven portion, the method comprising stitching the knot, enlarged knot, or woven portion to the first tissue with a needled second loop of the suture implant.

In one embodiment, the method includes multi-stitching the woven portion to the first tissue with a needled second loop of the suture implant. In one aspect, the method includes inserting a needled second loop of the suture implant through the first tissue up to at least one of: a knot of the needled second loop, enlarged knot of the needled second loop, or woven portion of the needled second loop. In one aspect, the method includes placing the first tissue through an aperture of a needled second loop of the suture implant before the multi-stitching.

In one embodiment, the method includes cutting the needled second loop and withdrawing the needle from the suture implant. In one aspect, the method includes forming a first cut strand and second cut strand from the cutting of the needled second loop. In one aspect, the method includes tying a knot with the first cut strand and second cut strand to secure the suture implant to the second tissue.

In one embodiment, the method includes cutting the first free end and second free end adjacent to the at least one splice after the first tissue is cinched to the second tissue. In one aspect, the method includes tying a knot in at least one of the cut first free end or cut second free end after the cutting.

In one embodiment, a member is slidably coupled with at least one of the adjustable first loop or adjustable third loop. Accordingly, the method includes coupling the member to the second tissue. In one aspect, the member is selected from a button, anchor, implant, needle, suture, screw, plate, bone anchor, orthopedic device, or combination thereof.

In one embodiment, the method includes forming a hole in the second tissue, and attaching the member to the second tissue in the hole. In one aspect, the hole has a narrower diameter portion closer to the first tissue and a larger diameter portion further from the first tissue, the hole has a ledge between the narrower diameter and larger diameter. Accordingly, the method can include locating the member on the ledge such that the member does not pull into the narrower diameter portion of the hole.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 1D shows the functional suture implant that has a single splice.

FIGS. 10A and 10B show an embodiment of a suture implant protection device that can protect the suture cords while being stored and while being sutured to the first tissue.

DETAILED DESCRIPTION

Figure 1A:
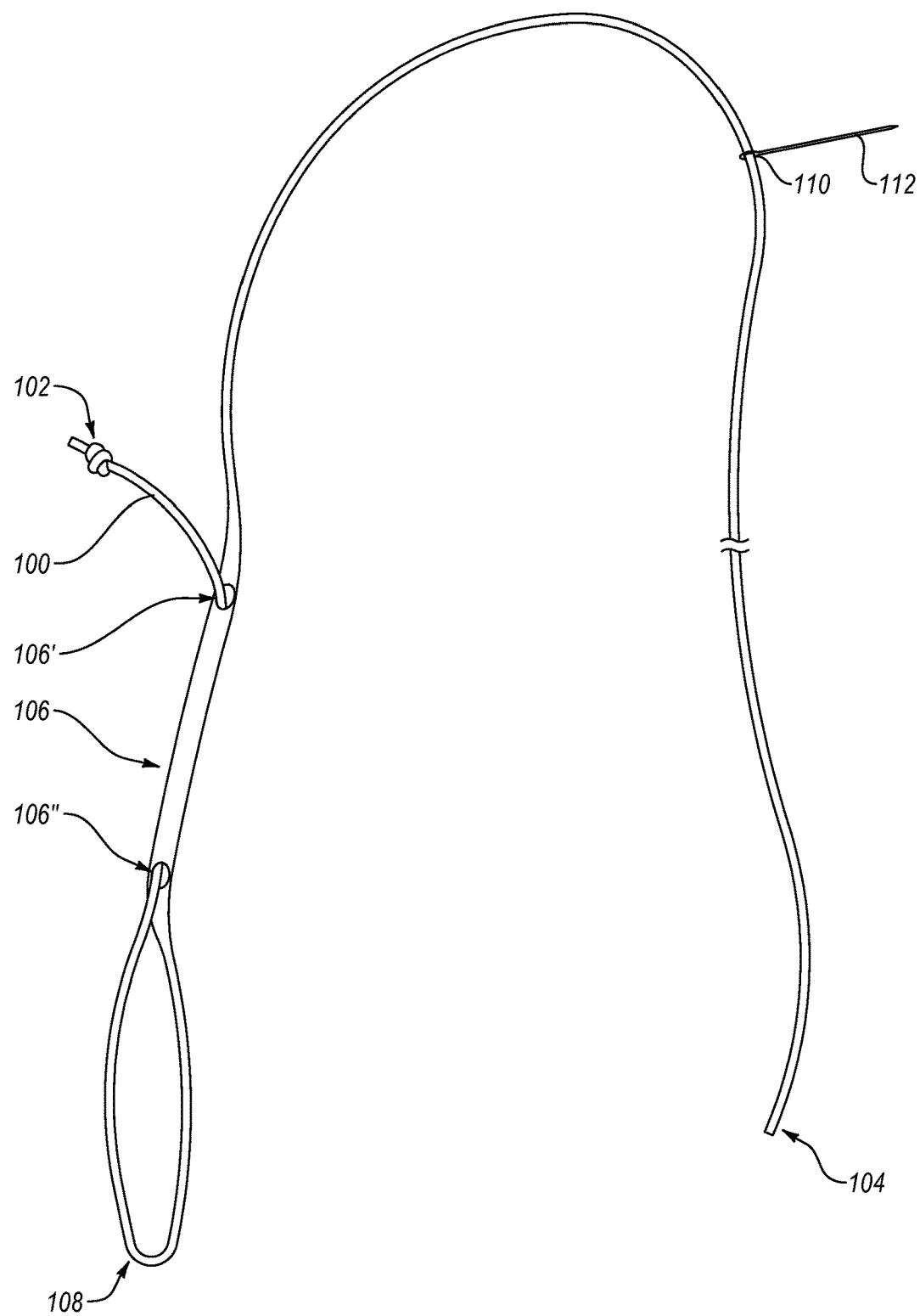
FIGS. 1A-1D show steps of forming an embodiment of a suture implant, where

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention is a suture implant that can be attached to a first tissue and cinch the first tissue (e.g., tendon, soft tissue, ligament, etc.) to a second tissue (e.g., bone, but can be tendon, soft tissue, ligament etc.) without the cinching causing the suture implant or anything else to slide through the first tissue. As a result, the suture implant provides a slideless suture that does not slide against the first tissue. The lack of sliding against the first tissue helps inhibit damage to the first tissue that may occur if the suture slides against the first tissue. Accordingly, the implant can cinch the first tissue and second tissue together without damaging the first tissue. Also, the suture implant can be adapted with a member, such as a button or bone anchor or needle for attachment to the second tissue such that the suture implant also does not slide against the second tissue during cinching. Here, the member is referred to as a button, but can be any suitable device, such as those described herein.

In one embodiment, the suture implant can be a self-cinching suture implant that can be stitched to the first tissue, such as via a whipstitch or other multi-stitch, and then connected to another tissue or another implant to cinch the first tissue to the other tissue or other implant. A button can be used for anchoring into the second tissue, where the button can have two spaced apart holes (e.g., apertures) that extend through the button, such as from a first side of the button to a second side of the button. The suture implant has a intertwined (e.g., interconnected such that two loops interconnect) adjustable double loop (e.g., there are two loops that are intertwined so as to form an adjustable loop that is cinched by pulling one or both free ends of each loop) with each loop passing through a unique button hole (e.g., one of the two button holes, which may also be referred to as apertures) so that both loops pass through separate button holes. The suture implant can include the two interconnected adjustable loops to form an adjustable interconnected double loop. Each adjustable loop can extend from the same side of a common splice. Each adjustable loop can have an adjustable cord that passes through the common splice, and extends from the common splice at the other end, where one cord of each loop forms a free end so as to have two free ends (e.g., one free end for each loop) and the other cord of each loop forms a needled loop having a needle. As such, pulling on one or both free ends chinches the interconnected adjustable double loop. Pulling one free end cinches the corresponding loop of the adjustable interconnected double loop, allowing for each loop of the adjustable interconnected double loops to be cinched and adjusted separately.

The needled loop can be stitched into the first tissue more than one time, such as a multi-stitch, which is exemplified by being whip-stitched into a soft tissue. Most often, the first tissue can be a soft tissue, such as a tendon or ligament or cartilage or meniscus. The button can be any bone anchor that can be fastened into a bone or tissue harder than the first tissue. Often, the second tissue that receives the button is a hard tissue or tissue harder than the first tissue, where sliding may be allowable without damaging the second tissue. The configuration of the suture implant can allow the suture implant to cinch the first tissue down to the second tissue and/or button on the suture implant without any suture cord sliding across or through the first tissue. This allows the placement of the second tissue to be adjacent to the first tissue without damaging the first tissue. This is performed so that the suture implant is coupled with bone (e.g., second tissue) or in a hole created in the bone to dock a tendon (e.g., first tissue) to the bone. During the cinching, the use of multiple stitches of the needled loop of the suture implant into the first tissue inhibits the suture implant from sliding against the first tissue. Accordingly, the configuration and use of the suture implant allows the ability to run a stitch through soft tissue (e.g., first tissue) and imbed the button in a second tissue (e.g., bone), and then to be adjusted and be tensioned by pulling both free ends of the interconnected adjustable double loop to cinch the needled loop toward the splice and button so as to cinch the first tissue and second tissues together.

FIG. 1A illustrates a suture cord 100 having two free ends—first free end 102 and second free end 104. FIG. 1A shows the suture cord 100 has a splice 106 formed therein so that the first free end 102 extends from a splice first end 106' and the second free end 104 extends from the splice first end 106', where the first loop 108 extends from the splice second end 106". Also shown is the suture cord 100 forming a first loop 108 by having the first free end 102 pass back through the splice second end 106" of the splice 106 and out from splice first end 106', and then the second free end 104 is passed through eyelet 110 of a needle 112. Here, it should be recognized that splice 106 can be formed by the first free end 102 being passed through a region of the suture cord 100 so that the first free end 102 is within the lumen formed into the suture cord 100 so as to form the splice 106. However, the splice 106 can be formed by the second free end 104 being passed through a region of the suture cord 100 so that the second free end 104 is within the lumen formed into the suture cord 100 so as to form the splice 106. Accordingly, the splice 106 has an opening at the splice first end 106' and an opening at the splice second end 106". As such, in one aspect the splice 106 is formed into the suture cord 100 closer to the first free end 102 or closer to the second free end 104 depending on which end is the sheath of the splice 106 and which end is the cord portion passing through the lumen of the sheath of the splice 106. It should be noted that the first loop 108 is adjustable when the first free end 102 is passed through the portion of the suture cord 100 that becomes the splice 106 so that when the first free end 102 is pulled the first loop 108 cinches down toward the splice second end 106".

Figure 1B:
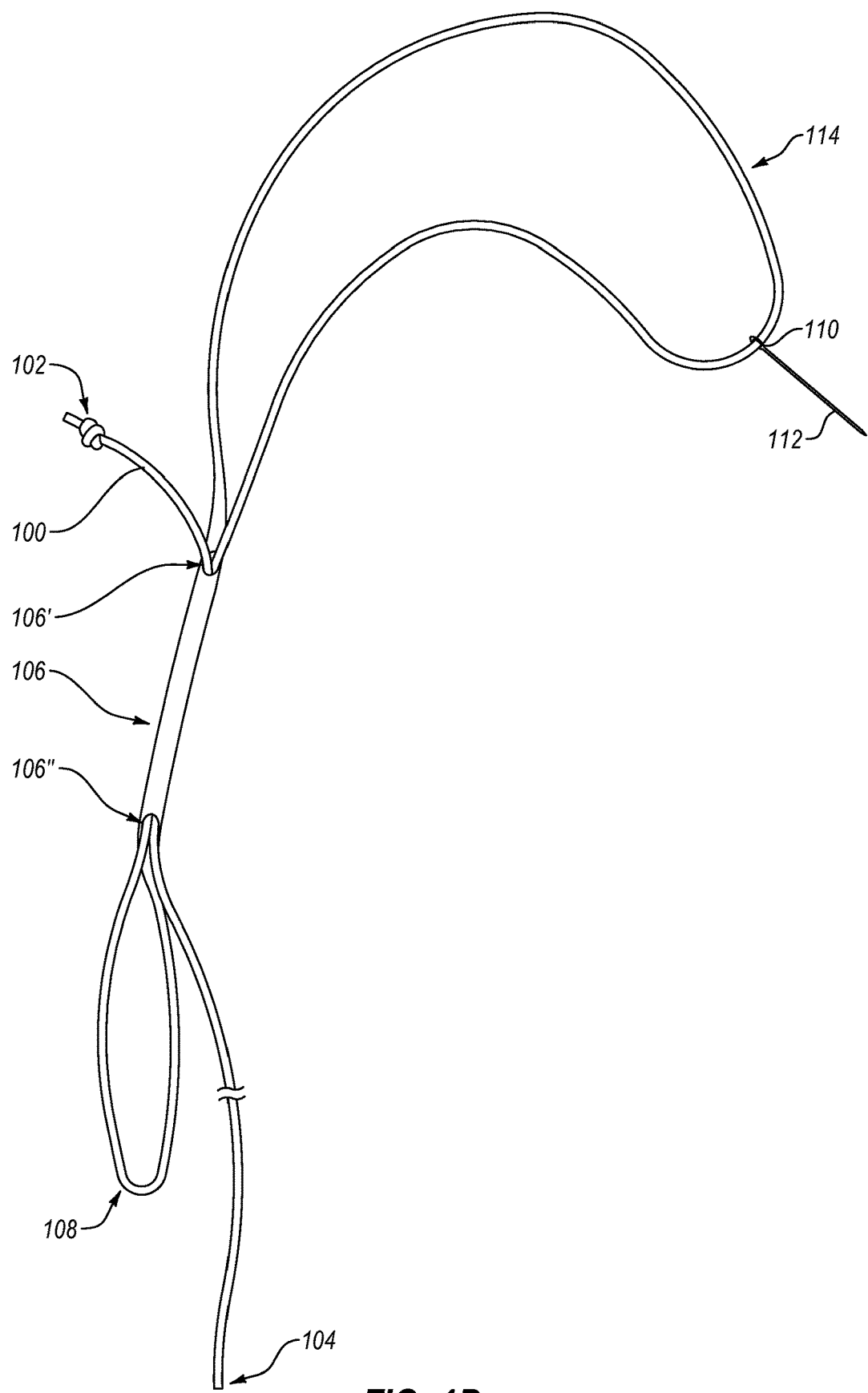

FIG. 1B shows the suture cord 100 forming a needled loop 114 (also referred to herein as the second loop because it is formed second) by having the second free end 104 pass back through the splice first end 106' of the splice 106 and out from the splice second end 106", where needled loop 114 has the needle 112 slidable thereon via the needle eyelet 110.

Figure 1C:
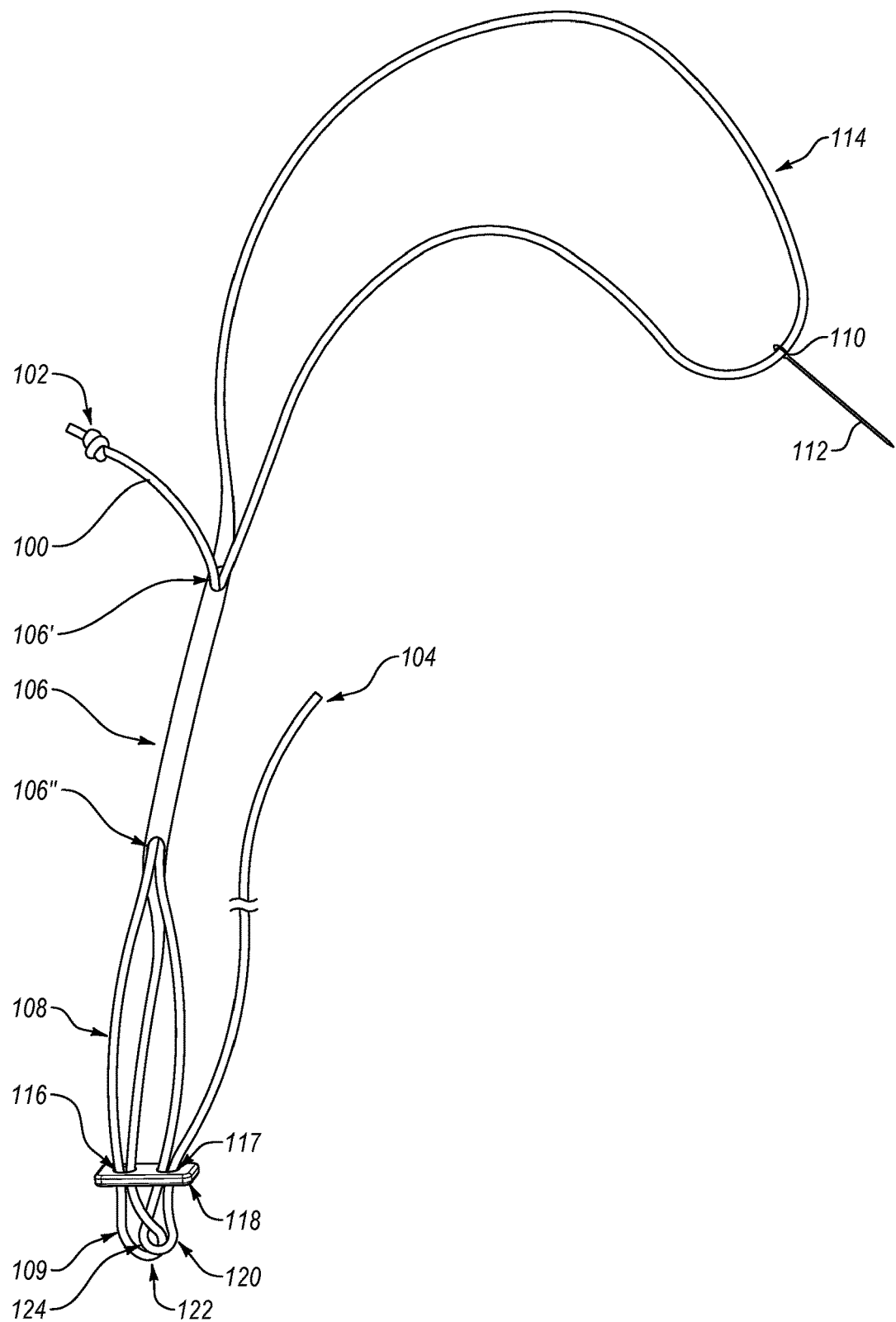

FIG. 1C shows the first loop 108 being passed through a first button hole 116 of a button 118 (e.g., enters on first side of button 118 and exits on second side of button 118) and the second free end 104 passing through a second button hole 117 of the button 118 (e.g., enters on first side of button 118 and exits on second side of button 118). FIG. 1C also shows the second free end 104 passing through the loop portion 109 of the first loop 108 that is protruding from the first button hole 116 of the button 118 (e.g., from second side of button 118) opposite of the splice 106, and then the second free end 104 is passing back through the second button hole 117 of the button 118 (e.g., enters on second side of button 118 and exits on first side of button 118). As such, the second free end 104 is passing through the loop portion 109 of first loop 108 protruding from the first button hole 116 of the button 118 opposite of the splice 106 and then the second free end 104 is passing back through the second button hole 117 of the button 118, which forms the adjustable interconnected double loop 122 from the adjustable first loop 108 and adjustable third loop 120, which together form the adjustable interconnected double loop 122. The point where adjustable first loop 108 and adjustable third loop 120 interconnect is interconnection 124.

Figure 1D:
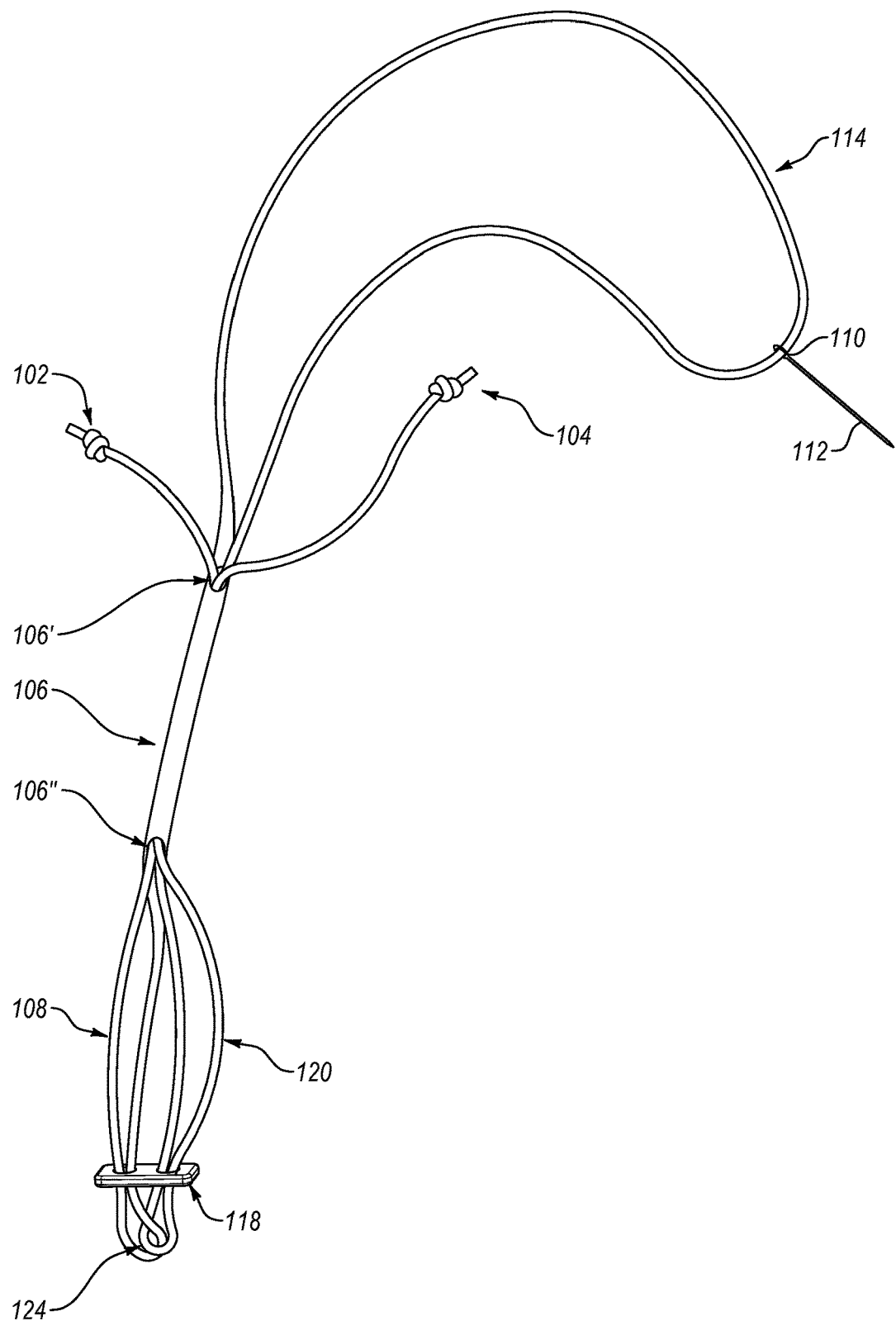

FIG. 1D shows the second free end 104 passing again into the splice second end 106" of the splice 106 and out of splice first end 106', which fully forms adjustable loop 120 (e.g., referred to herein as the third loop because it is formed third). Accordingly, the first free end 102 can be pulled to cinch adjustable first loop 108 (e.g., first loop) and where second free end 104 can be pulled to cinch adjustable third loop 120 (e.g., third loop), where pulling at least one of the first free end 102 and/or the second free end 104 can cinch the adjustable interconnected double loop 122.

Figure 1E:
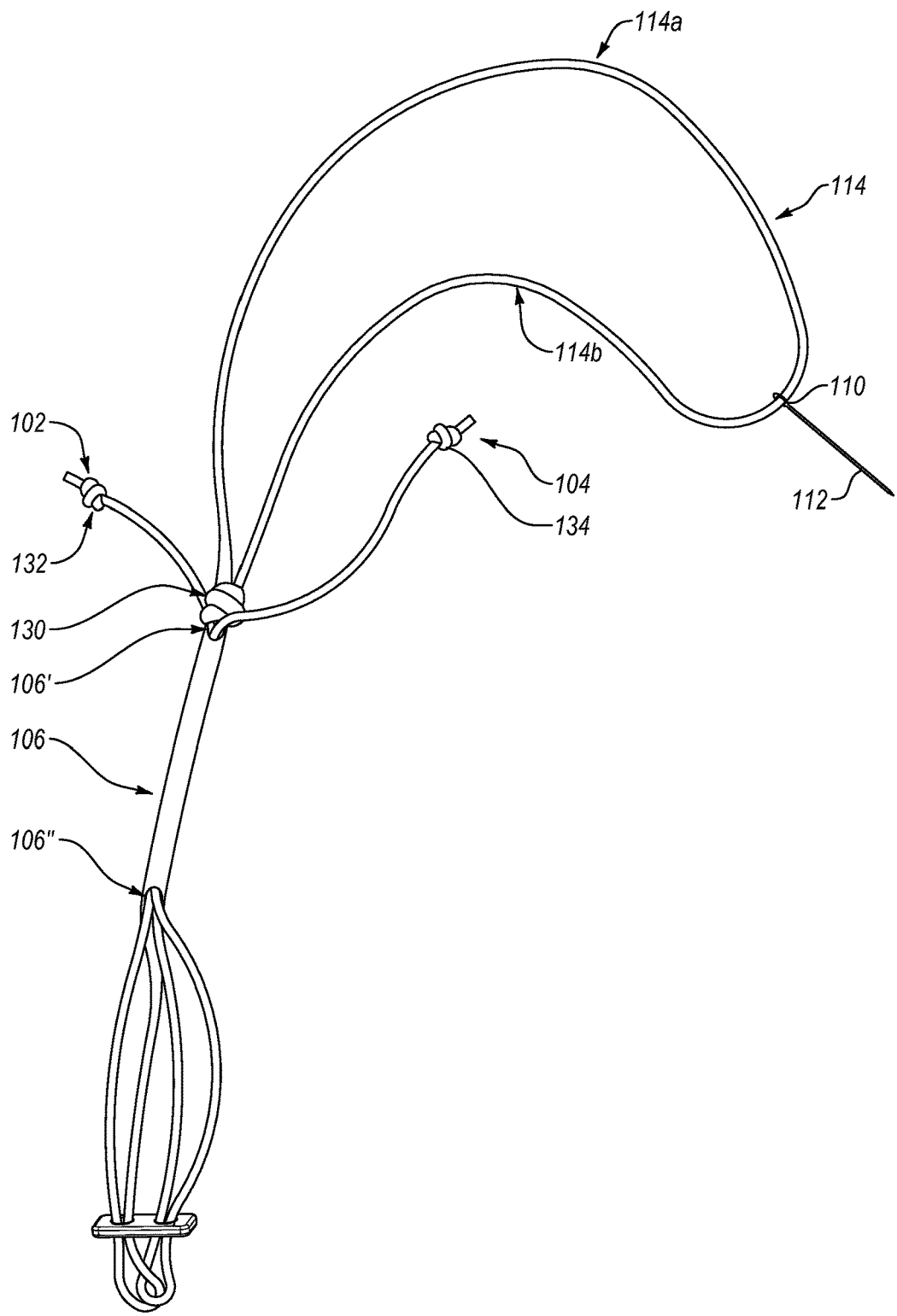
FIG. 1E shows another embodiment of the suture implant.

FIG. 1E shows an enlarged section of the splice 106 and needled loop 114 (e.g., second loop). As shown, an optional knot 130 is formed on the needled loop 114 and/or on the splice 106 so that the needled loop 114 cannot be pulled through the splice 106. Thus, needled loop 114 can be un-adjustable. The knot 130 may be formed at any time, preferably before forming loop 120. However, by formation of the splice 106 and formation of loop 120, it is difficult to cinch the needled loop 114. On the other hand, the knot 130 can ensure that the needled loop 114 is not adjustable. FIG. 1E shows a close-up of knot 130. Knot 130 can be a premade knot that is on the suture implant and placed so that needled second loop 114 does not slide relative to the splice 106 or implant, such as relative to the splice 106, first free end 102, and/or second free end 104. In one aspect, knot 130 is on the first strand 114a side of loop 114. In one aspect, knot 130 is on the second strand 114b side of needled second loop 114. In one aspect, knot 130 is on both the first strand 114a and second strand 114b. In one aspect, knot 130 is on splice 106 with at least one of the first strand 114a and/or second strand 114b. For example, the knot 130 can be on the splice first end 106'. When included on one or more of first strand 114a and/or second strand 114b, it inhibits free ends 102 and/or 104 from being pullable to draw or shorten needled loop 114 or draw strands 114a and/or 114b into the splice 106. This can be helpful during formation of the suture implant. Accordingly, needled loop 114 can be affixed to the tissue T1 by having the needled loop 114 pulled through the tissue T1 up to the knot 130, and thereby knot 130 can inhibit the splice 106 from being pulled into a hole in the tissue T1 through which the needled loop 114 passes through. Upon multi-stitching with needled loop 114, the knot 130 rests against the tissue T1. Thus, during cinching, the strands 114a and 114b are fixed relative to the splice 106, and thereby first loop 108 and third loop 120 are cinched by pulling free ends 102 and 104 to draw the first tissue T1 to the button 118, such as described herein.

Accordingly, FIGS. 1A-1D show the suture cord 100 has a splice 106 so that the first free end 102 extends from the splice first end 106' and second free end 104 extends from the splice first end 106'. The suture cord 100 also forms needled loop 114 extending from the splice first end 106' of the splice 106, where needled loop 114 has the needle 112 slidable thereon. The suture cord 100 also has first loop 108 extending from the splice second end 106" and being passed through a first button hole 116 of a button 118 and loop 120 (e.g., formed from free end 104 passing through loop portion 109 of loop 108) extending from the splice second end 106" and being passed through a second button hole 117 of a button 118 around the first loop 108 back through the second button hole 117 and then back through the splice 106 by entering the splice second end 106" and exiting the splice first end 106'. Loop 108 and loop 120 are intertwined or interconnected so that the loop portion 109 of first loop 108 and third loop 120 are linked such that each passes through the other once to form the intertwined junction 124 and form interconnected adjustable double loop 122. The button 118 is slidable on loops 108 and 120 and thereby slidable relative to interconnected adjustable double loop 122. Also, knot 130 is shown. Optionally, free end 102 can have knot 132 and free end 104 can have knot 134.

FIGS. 2A-2E show steps for methods of using the suture implant to suture a first tissue T1 to a second tissue T2, where the first tissue T1 can be a soft tissue (e.g., cartilage meniscus, tendon, ligament, muscle, or other), and the second tissue T2 can be a hard tissue such as bone or a tissue harder than the first tissue T1.

Figure 2A:
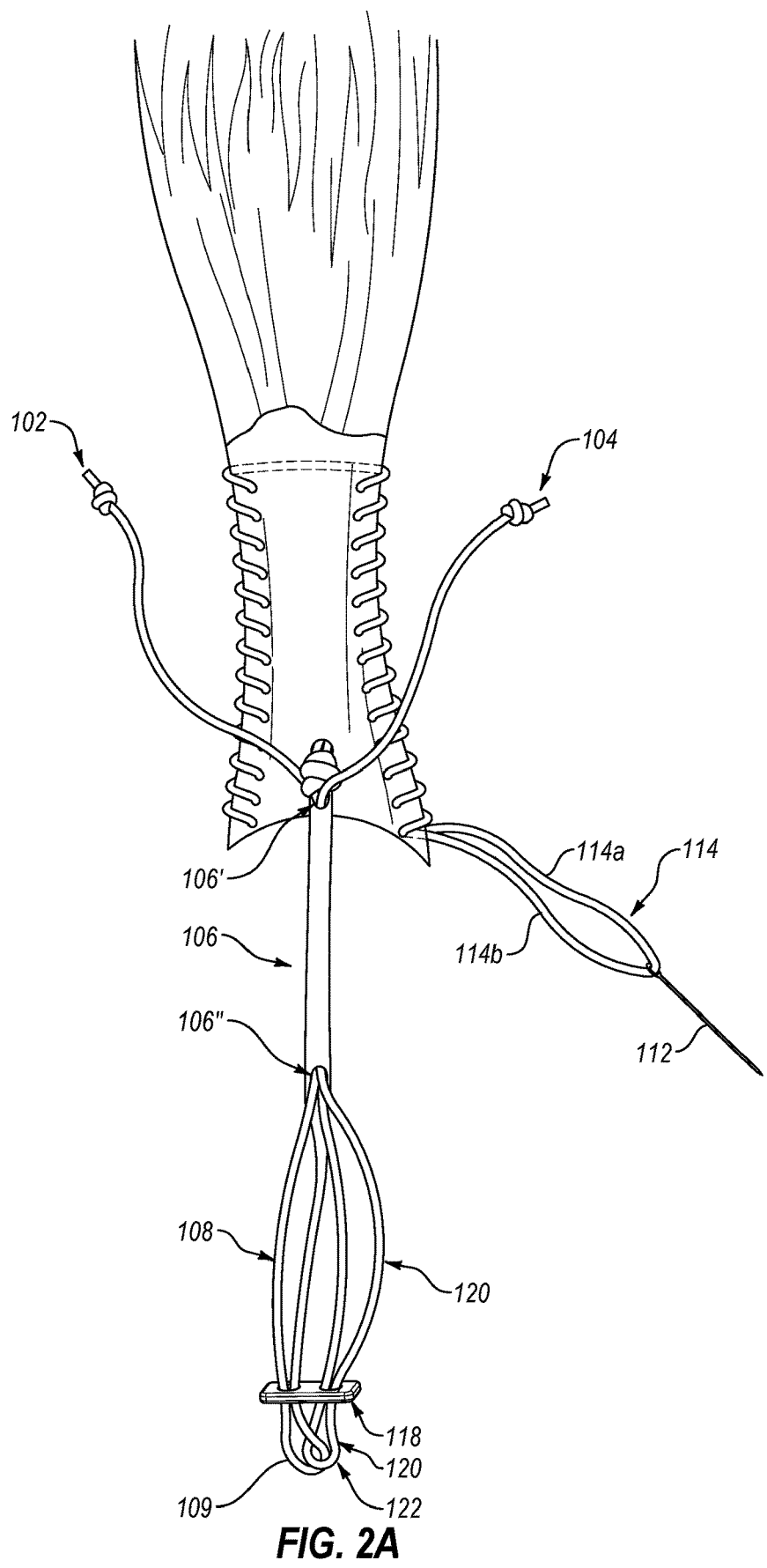
FIGS. 2A-2E shows steps for a method of cinching a first tissue to a second tissue with the implant formed from the steps of FIGS. 1A-1D, where the cinching is performed without the suture implant sliding through or against the first tissue.

FIG. 2A shows needled loop 114 having the needle 112 being multi-stitched into the first tissue T1. A whipstitch is an example of a multi-stitch.

Figure 2B:
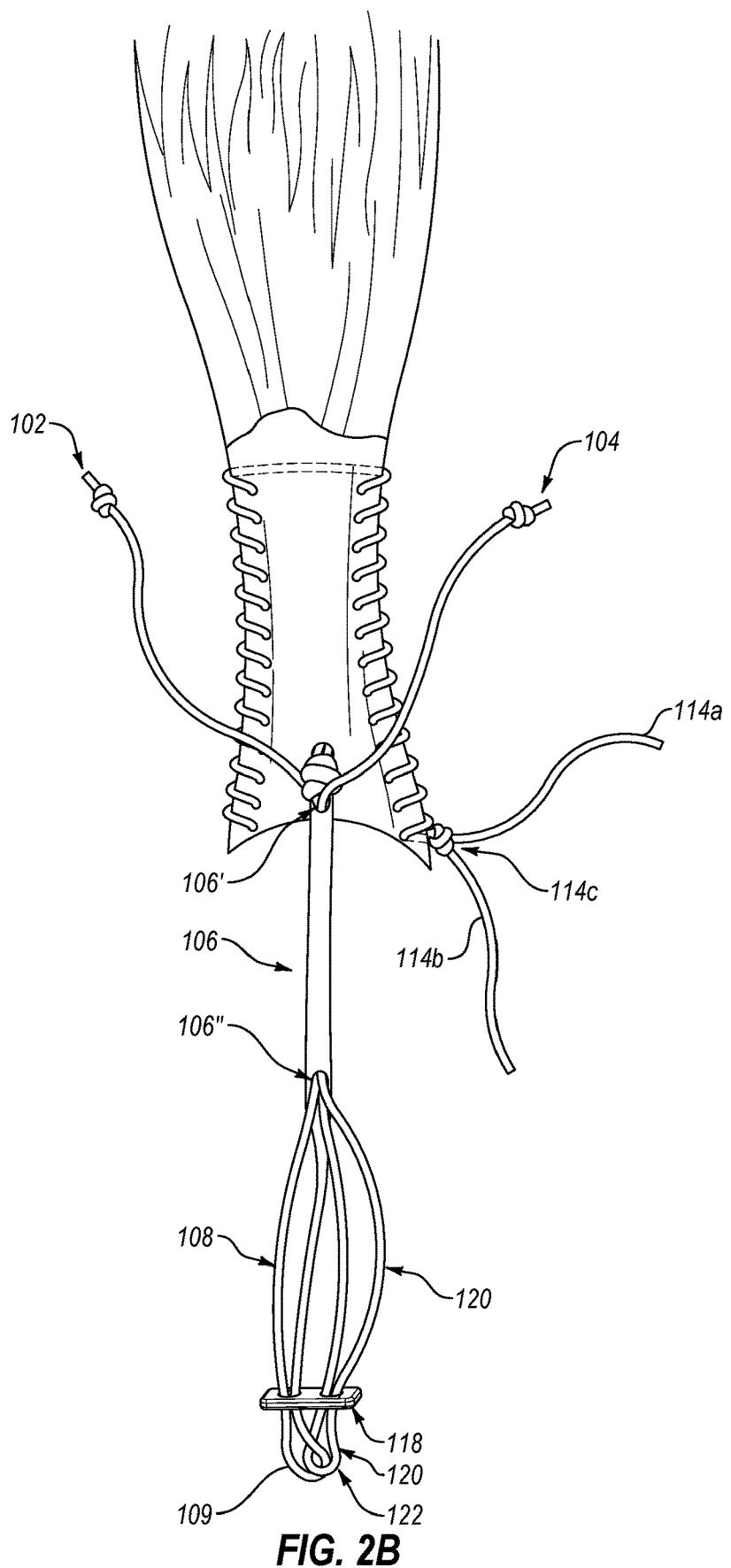

FIG. 2B shows needled loop 114 being cut to form strands 114a and 114b and the needle 112 is removed. Optionally, needled loop 114 is tied into knot 114c before being cut. As such, before or after cutting needled loop 114, first strand 114a and second strand 114b (e.g., which is shown after being cut into strand 114a and strand 114b) can be tied together into knot 114c on the first tissue T1, which locks the suture implant to T1 such that suture implant is fixed to the first tissue T1. This allows for pulling the suture implant to pull the first tissue T1 without the suture being pulled through the first tissue T1 or rubbing against the first tissue T1, which inhibits damage from the suture tearing a hole in the first tissue T1. Optionally, strands 114a and 114b are cut to leave knot 114c at the first tissue T1.

Figure 2C:
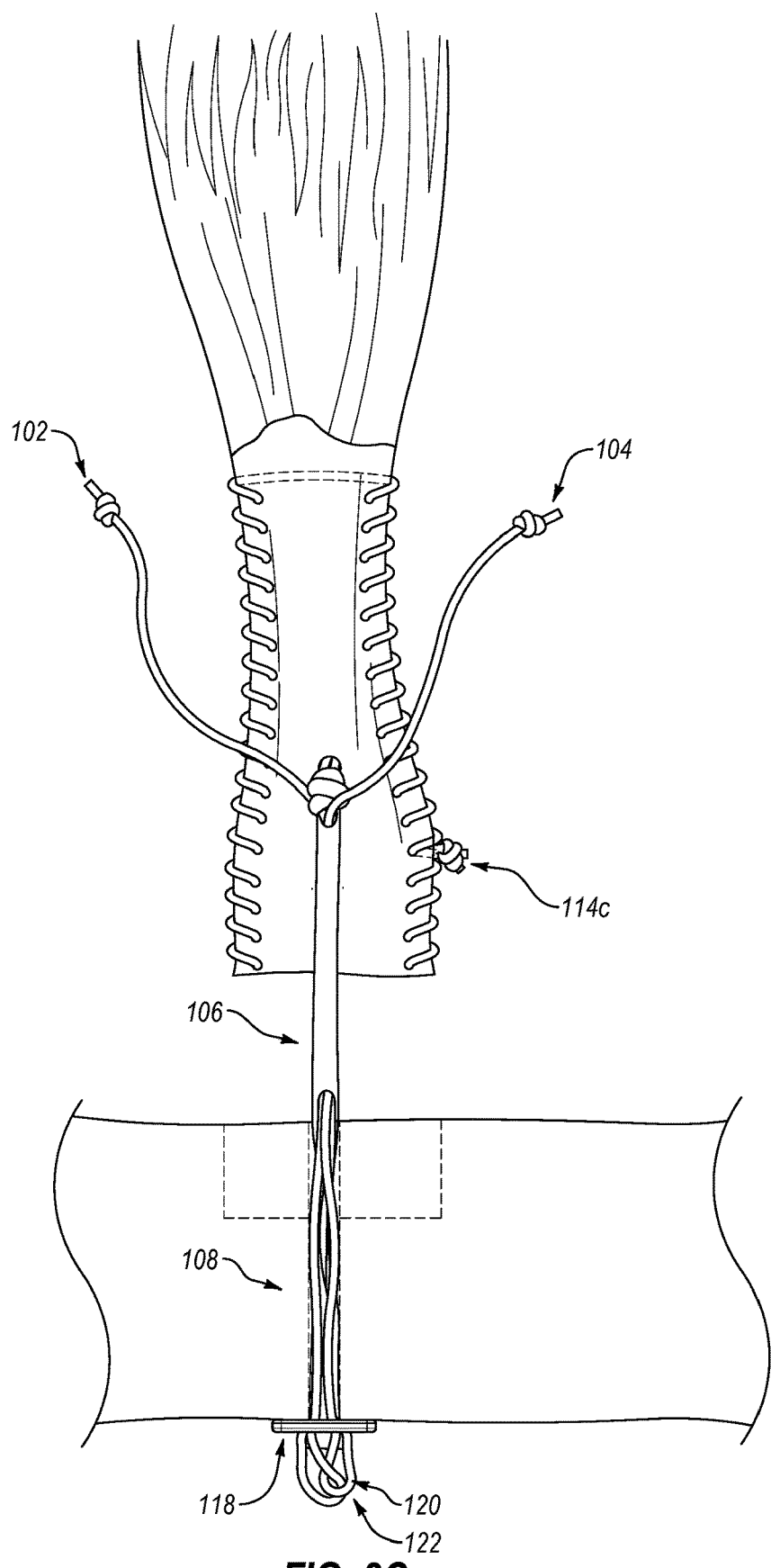

FIG. 2C shows a second tissue T2 being prepared to receive the button 118 (e.g., or anchor or the like) of the suture implant, which can be done by forming a hole into the second tissue T2 (e.g., bone) and fixing the button 118 therein; however, other means of fixing a button or anchor to a bone can also be performed.

Figure 2D:
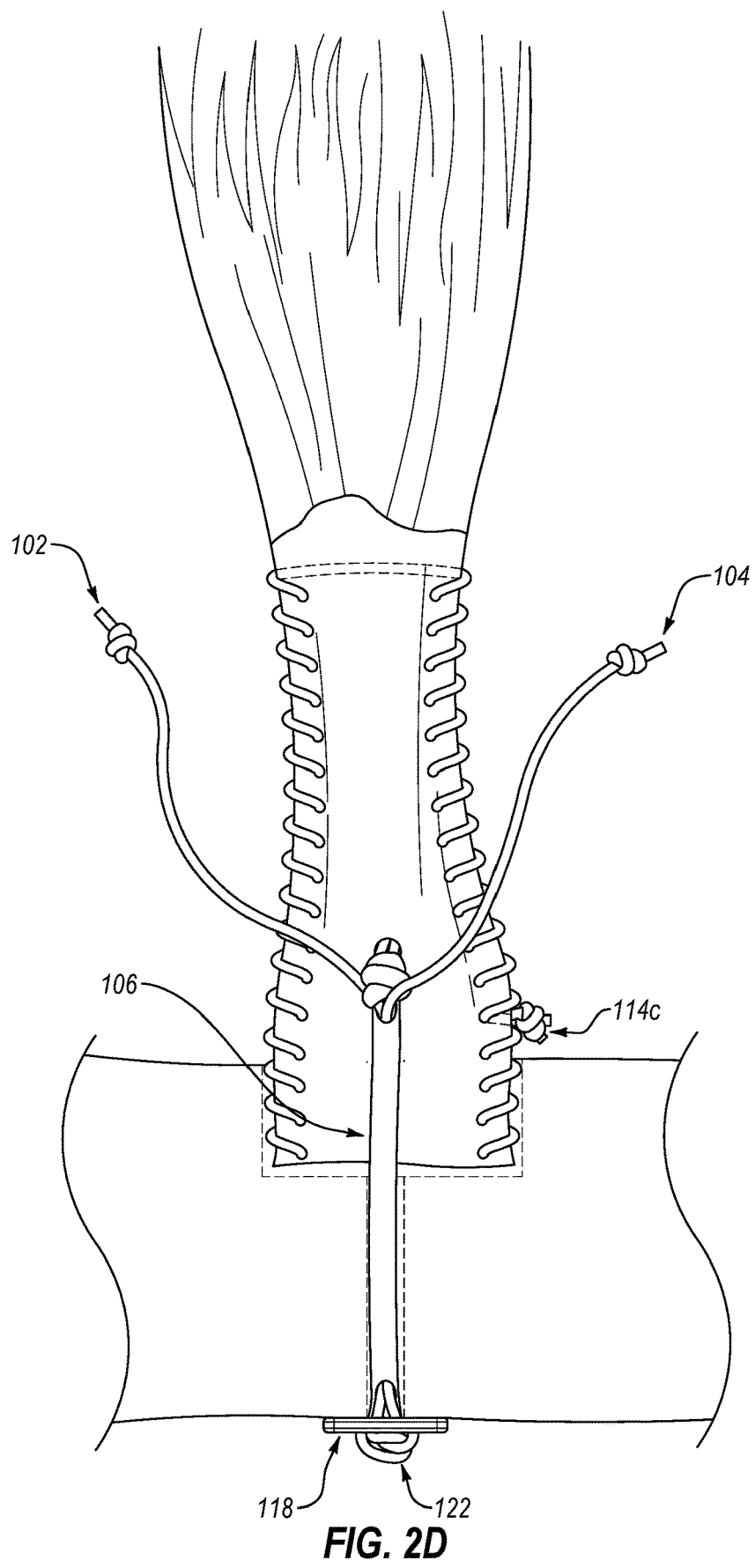
Figure 2E:
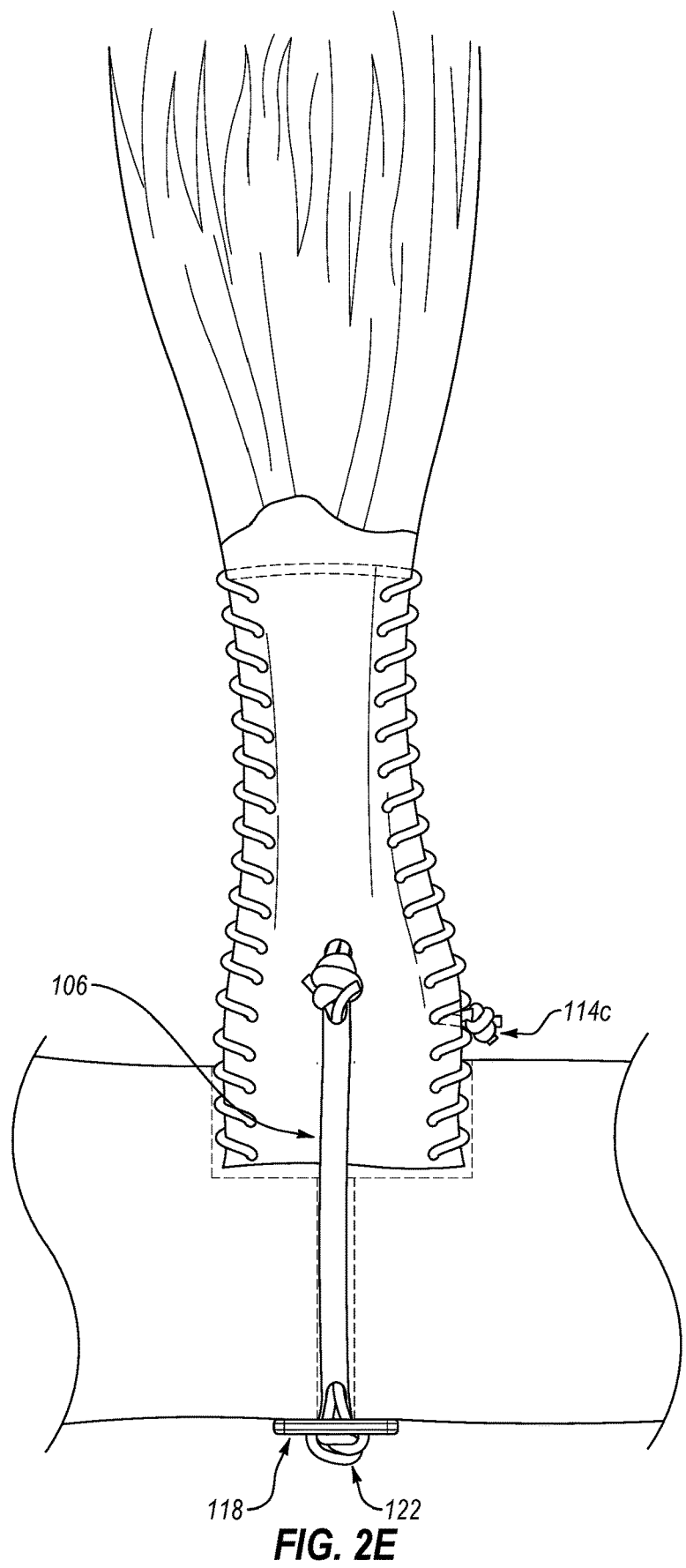

FIG. 2D shows the free ends 102 and 104 being pulled to cinch the first tissue T1 and the splice 106 toward the button 118, and thereby splice 106 and the first tissue T1 are cinched to (e.g., optionally into) the second tissue T2. The loops 120 and 108 also cinch down by pulling free ends 102 and 104, which cinches the adjustable interconnected double loop 122 down so the first tissue T1 is drawn to the second tissue T2. Free ends 102 and 104 can be pulled independently or simultaneously, or one pulled, and then the other pulled, and repeated in an alternating format, or combinations thereof.

FIG. 2D shows the cords of free ends 102 and 104 are cut to leave the implant linking the first tissue T1 to the second tissue T2 with the splice 106 therebetween with the button 118 in the hole of the second tissue T2. Also, knots can be formed at the cut ends of free ends 102 and 104 so that these free ends do not pull back through the splice 106.

Accordingly, needled loop 114 can be affixed to the tissue T1 by having the needled loop 114 pulled through the tissue T1 up to the knot 130, and thereby knot 130 can inhibit the splice 106 from being pulled into a hole in the tissue T1 through which the needled loop 114 passes through. Upon multi-stitching, the knot 130 rests against the tissue T1. Thus, during cinching, the strands 114a and 114b are fixed relative to the splice 106, and thereby loops 108 and 120 are cinched by pulling free ends 102 and 104, respectively, thereby cinching the adjustable interconnected double loop 122 to draw the first tissue T1 to the button 118, thereby the first tissue T1 to the second tissue T2, such as described herein.

The implants described herein can be used similarly to the other implants of the incorporated references. Here, the needle 112 on the needled loop 114 can be used to whip-stich or other multi stich a first tissue T1 (e.g., tendon). Optionally, the first tissue T1 can be passed through the aperture of the needled second loop 114, and then the needle 112 can penetrate through the first tissue T1 for multi-stitching. In any event, the needled loop 114 is fixed to a first tissue T2 and the adjustable interconnected double loop 122 (e.g., interconnected double loop formed from the first loop 108 interconnected with the third loop 120) is fixed to a second tissue T2 via the button 118 on the adjustable double loop 122. The button 118 can be attached to the second tissue T2 as known in the art. Various configurations of the button 118, such as a bone anchor, can facilitate such attachment. Also, the button 118 on the adjustable loop 122 may be a needle to attach the adjustable double loop 122 to a soft tissue, such as by whip-stitching similar to the needled loop 114. After the needled loop 114 (e.g., which can be formed into a fixed loop that does not cinch) is attached to a first tissue T1 and the adjustable interconnected double loop 122 is attached to a second tissue T2, the tensioning strands at first end 102 and second end 104 attached to the adjustable interconnected double loop 122 can be tensioned and pulled so as to pull the adjustable interconnected double loop 122 closed so as to cinch the first tissue T1 and second tissue T2 together.

The suture implant can be used in various medical procedures where suturing can be used. In some examples, the suture implant can be used to connect a softer tissue to a harder tissue, such as connecting a tendon to bone. In some instances, the suture implant can be used to connect two soft tissues that may or may not be the same, such as connecting a part of a meniscus to another part of a meniscus, or connecting two hard tissues (e.g., connecting two bone pieces together). In any event, the use of the suture implant can be performed as described herein. The examples provided herein are not limiting, and are merely demonstrative of the capabilities of the uses of the suture implant.

Any button described herein can be any anchor, plate, screw, needle or other member, such as a member that aids in facilitating attachment to another tissue, such as bone. When a needle, the first loop 108 or the third loop 120 or the adjustable interconnected double loop 122 may pass through the needle eyelet 110, and the needle 112 may be multi-stitched to a second tissue T2 similarly to how the needled loop 114 is multi-stitched to the first tissue T1, except that the suture cord 100 can slide through the eyelet 110 while cinching the first tissue T1 to the second tissue T2.

In one embodiment, a splice can be a conduit that is formed within a suture cord such that the suture cord forms the conduit as a lumen within the cord body with another portion passing through the lumen. The conduit of the splice serves as a conduit for another suture cord or portion of the same suture cord. The splice may also be a sleeve or other member coupled or attached to the suture cord that provides a conduit for another suture cord to pass through.

In some embodiments, a splice 106 can be shared between two loops, such as a fixed needled loop (e.g., second loop, 114) and adjustable loops (e.g., first loop 108, third loop 120 or adjustable interconnected double loop 122), two adjustable loops or two fixed loops. Alternatively, a splice 106 may be split into two separate splices, such as a splice for the fixed loop and a splice for the adjustable loop, or the like.

The implants described herein can be prepared with a single cord. However, multiple cords can also be used to prepare the implant.

In one embodiment, a method of cinching two tissues together can be performed with the suture implant devices described herein. Step 1: take the fixed loop (e.g., 114) and put the fixed loop around the first tissue (e.g., tendon, T1) and whip-stitch from the fixed loop up the first tissue. In one aspect, the practitioner can whip-stitch the first tissue and then stitch up the first tissue one centimeter (or a suitable distance) and then stitch down the first tissue that one centimeter (or same suitable distance to the starting point). This stitching can lock the fixed loop side of the implant into place on the first tissue. Then after the whipstitch is in the first tissue, the practitioner can cut the needle off of the fixed loop to generate two free ends. The two free ends can be connected together again via being tied or an anchor member or clasp clamping the two strands together. The button is then connected to the second tissue (e.g., T2), whether it is a hard tissue or a soft tissue. The hardness can determine the configuration of the button being a needle or a bone anchor. When a tissue, the button can be a needle and stitch (e.g., whip-stitch) the second tissue. When a bone, the button can be a bone anchor that is inserted into the second tissue. In one aspect, the practitioner can drill a hole in the bone to receive the button. Once the implant is attached to the first and second tissue, the tensioning strands (e.g., 102 and 104) can be pulled so as to close the adjustable loop (e.g., interconnected loop 122) and cinch the first tissue and second tissues together. This can suck the first tissue into the socket of the second tissue.

Figure 3:
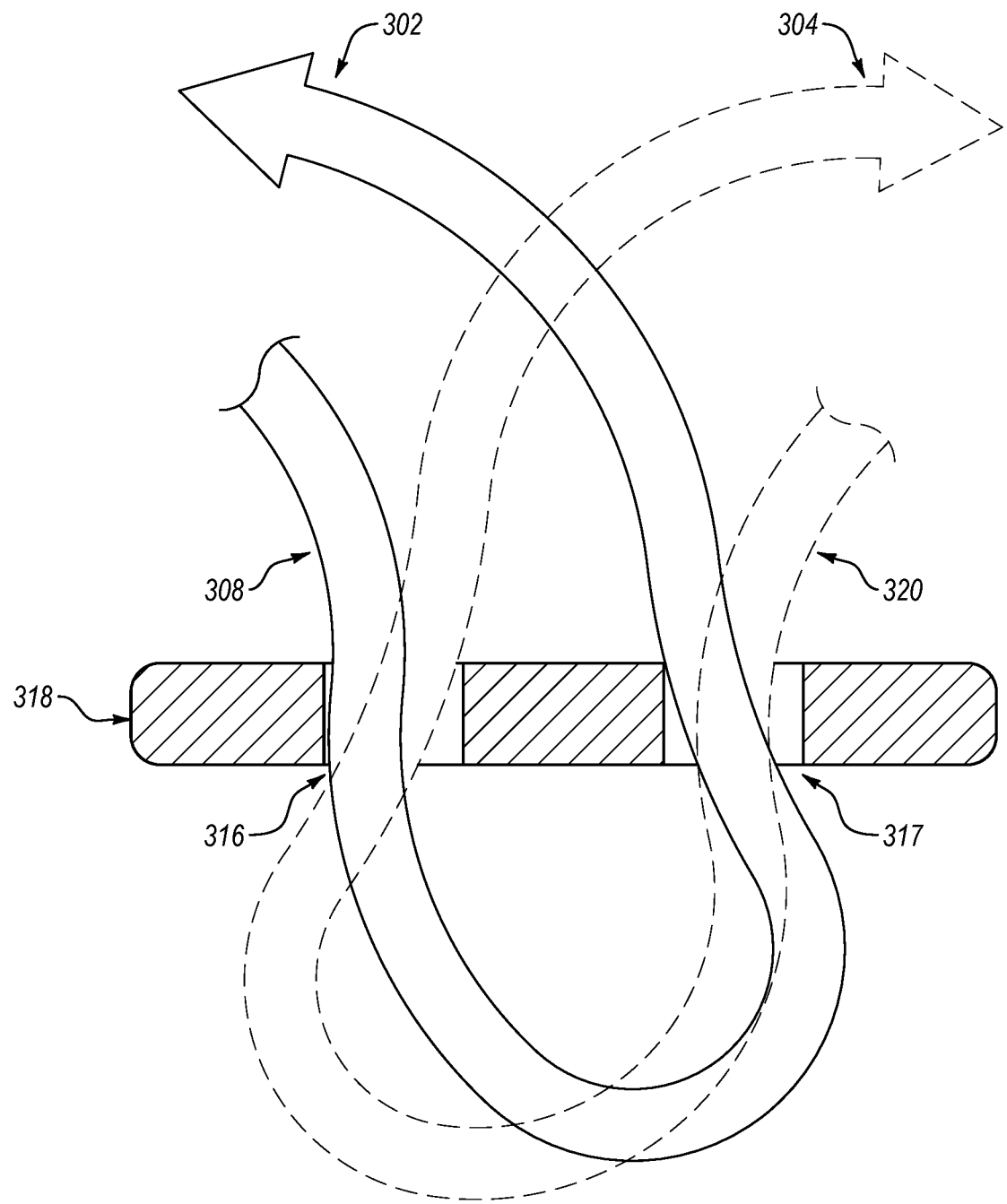
FIG. 3 shows an embodiment of a configuration for slidably coupling a button on the suture implant, which configuration can be used for all of the embodiments illustrated and described herein.

In one embodiment, FIG. 3 shows an alternative way for the suture implant to have the loops 308 and 320 slidably couple with the button 318. Here, loop 308 (solid line) is formed by passing the free end 302 through the first button hole 316 of the button 318 from the first side to the second side and then through the second button hole 317 of the button 318 from the second side to the first side. Loop 320 (dashed line) is formed by passing the free end 304 through the second button hole 317 of the button 318 from the first side to the second side and then through the first button hole 316 from the second side to the first side. The rest of the implant can be prepared as described in FIGS. 1A-1E. This configuration can be applied to any of the suture implant embodiments described herein.

Figure 4:
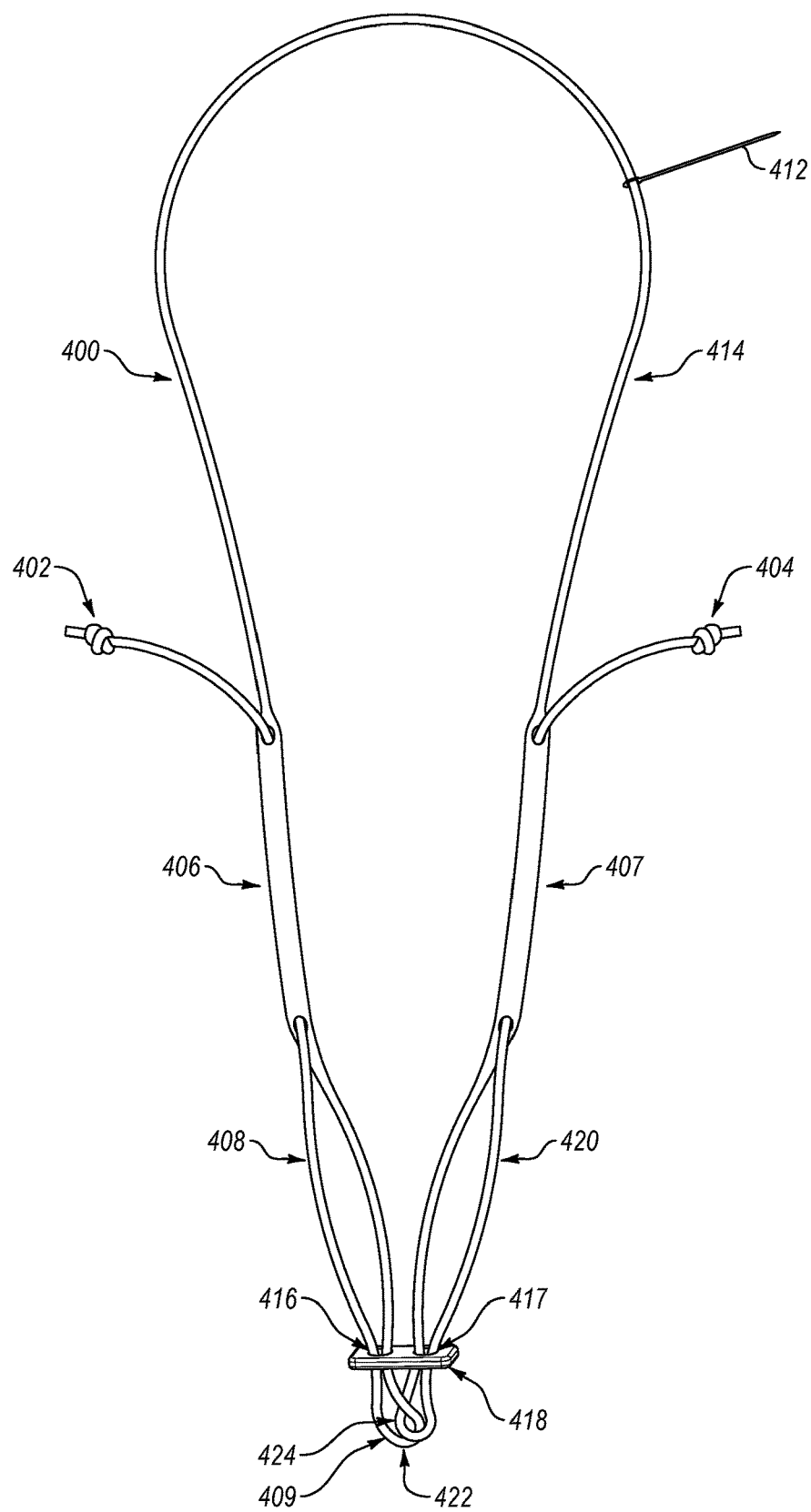
FIG. 4 shows an embodiment of a suture implant that has two separate splices that can be used in the method steps of FIGS. 2A-2E.

FIG. 4 shows another embodiment of a suture implant formed from a suture cord 400. Here, the adjustable first loop 408 is formed by passing the first free end 402 through a portion of the suture cord 400 so that the first splice 406 is formed as shown. Instead of the second free end 404 being passed back through the first splice 406 (or 106 in FIG. 1), it is used to form a second splice 407 by passing the second free end 404 through a portion of the suture cord 400 so that the second splice 407 is formed. However, before formation of the second splice 407, the first loop 408 is passed through a first button hole 416 of a button 418 so that a first loop portion 409 of the first loop 408 protrudes from the first button hole 416, and then the second free end 404 is passed through a second button hole 417 of the button 418 then through and around the first loop portion 409 to form interconnection 424 and then back through the second button hole 417 of the button 418 and then through the portion of the suture cord 400 to form the second splice 407. Now, there are two splices 406 and 407 as per FIG. 4. Here, it is noted that the needled loop 414 is a large loop having the needle 412 between the first splice 406 and second splice 407. The passing of the second free end 404 through the second button hole 417 and first loop portion 409 and back through the second button hole 417 the other direction and back through the suture cord 400 to form the second splice 407 also forms the second adjustable loop 420. Together the adjustable first loop 408 and the adjustable second loop 420 form the adjustable interconnected double loop portion 422. The adjustable interconnected double loop portion 422 is similar to the adjustable interconnected double loop 122; however, the adjustable interconnected double loop portion 422 is a portion of the large needled second loop 414.

Figure 5A:
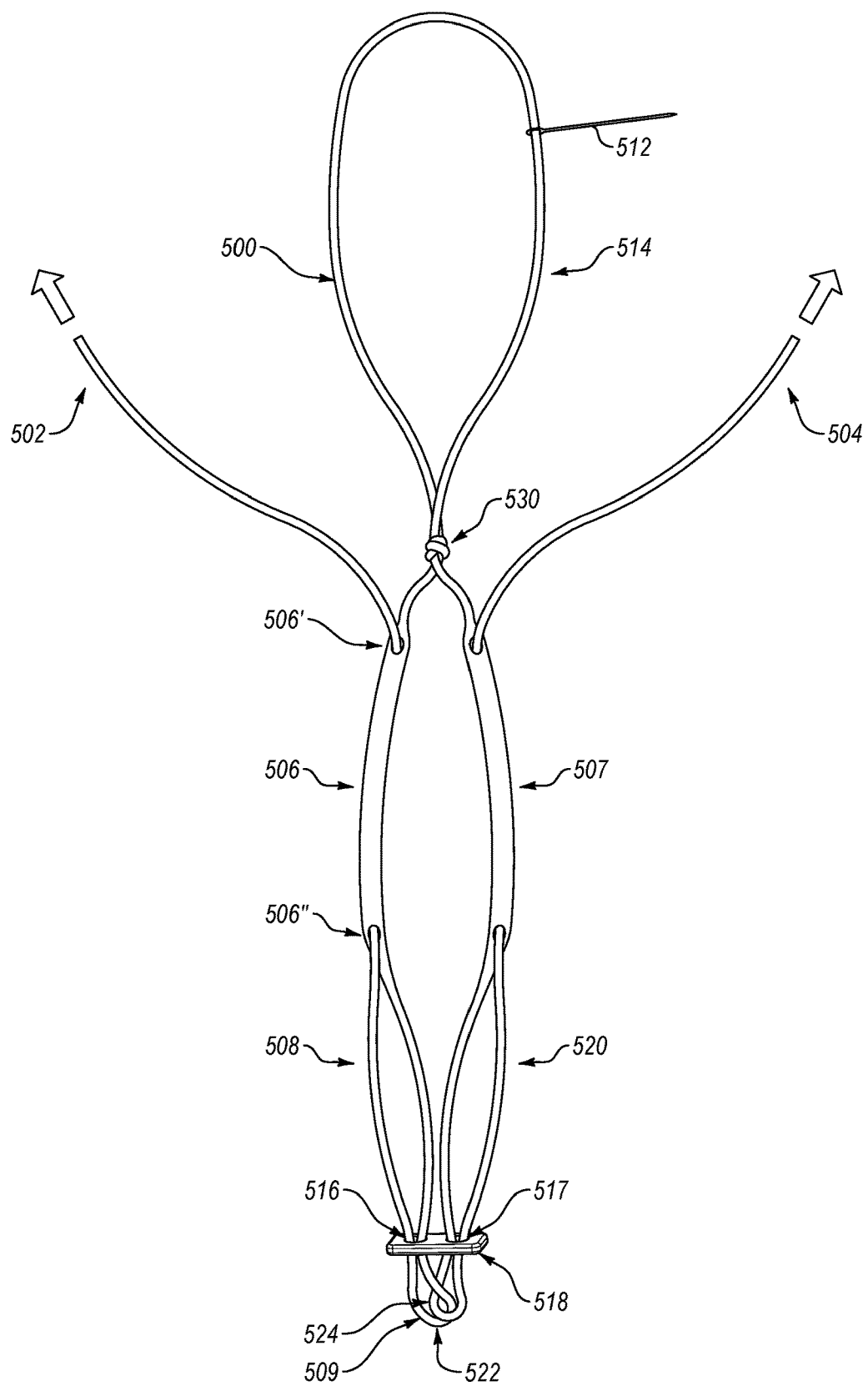
FIGS. 5A-5C show an alternate embodiment of suture implants based on the embodiment of FIG. 4.

FIG. 5A shows an embodiment of a suture implant that can be formed with a suture cord 500 similar to as shown in FIG. 4. Here, the adjustable first loop 508 is formed by passing the first free end 502 through a portion of the suture cord 500 so that the first splice 506 is formed as shown. Instead of the second free end 504 being passed back through the first splice 506 (or 106 in FIG. 1), it is used to form a second splice 507 by passing the second free end 504 through a portion of the suture cord 500 so that the second splice 507 is formed. However, before formation of the second splice 507, the first loop 508 is passed through a first button hole 516 of a button 518 so that a first loop portion 509 of the first loop 508 protrudes from the first button hole 516, and then the second free end 504 is passed through a second button hole 517 of the button 518 then through and around the first loop portion 509 to form interconnection 524 and then back through the second button hole 517 of the button 518 and then through the portion of the suture cord 500 to form the second splice 507. Now, there are two splices 506 and 507 as per FIG. 5A. Here, instead of the needled loop 514 being a large loop, a knot 530 is formed as shown to be between the first splice 506 and second splice 507. The knot 530 can be formed by tying the suture cord 500 to itself to form the needled loop 514 as well as the adjustable interconnected double loop 522. Here, the adjustable interconnected double loop 522 includes the first loop 508 and third loop 520 as well as the two splices 506, 507 up to the knot 530. However, the knot 530 may be an anchor, clip, tie, or other feature, whether formed from the suture cord 500 or formed from another member, which links the suture cord 500 together as shown to form the needled loop 514 separate from the adjustable interconnected double loop 522. Cinching is obtained by pulling the free ends 502, 504 in the direction of the arrows.

Figure 5B:
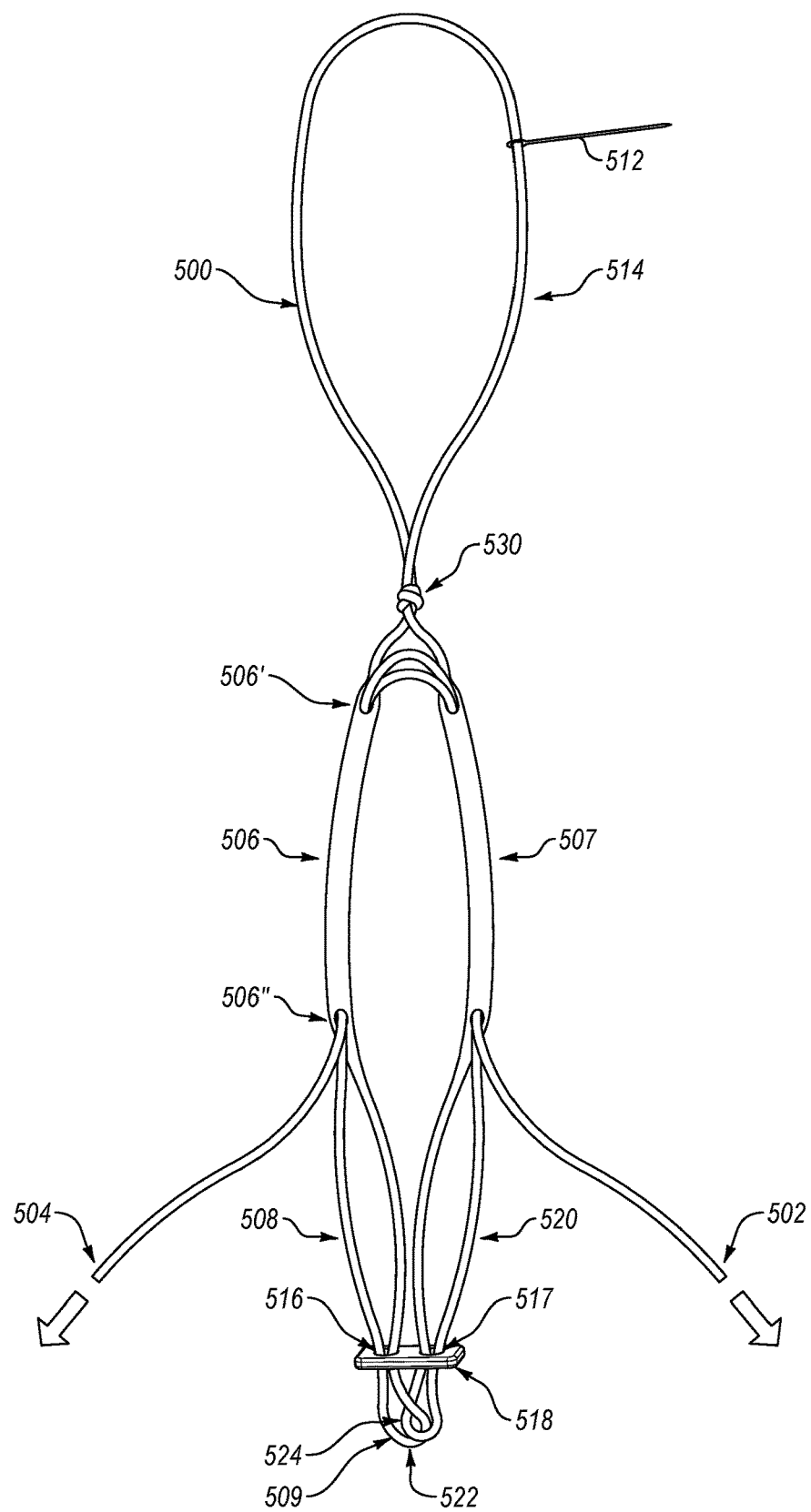

FIG. 5B shows an embodiment that gives the option of pulling the free ends 502, 504 in a different direction compared to FIG. 5A. Here, the suture implant is formed as described in connection with FIG. 5A. Then, first free end 502 is passed through the second suture 507 from the second suture first end 507' through the second suture 507 and out from the second suture second end 507". Optionally, the first free end 502 is passed through the knot 530 before the second splice 507. Otherwise, the knot 530 can be formed to be at the second suture first end 507'. Then, second free end 504 is passed through the first suture 506 from the first suture first end 506' through the first suture 506 and out from the first suture second end 506". Optionally, the second free end 504 is passed through the knot 530 before the first splice 506. Otherwise, the knot 530 can be formed to be at the first suture first end 506". Here, cinching is obtained by pulling the free ends 502, 504 in the direction of the arrows.

Figure 5C:
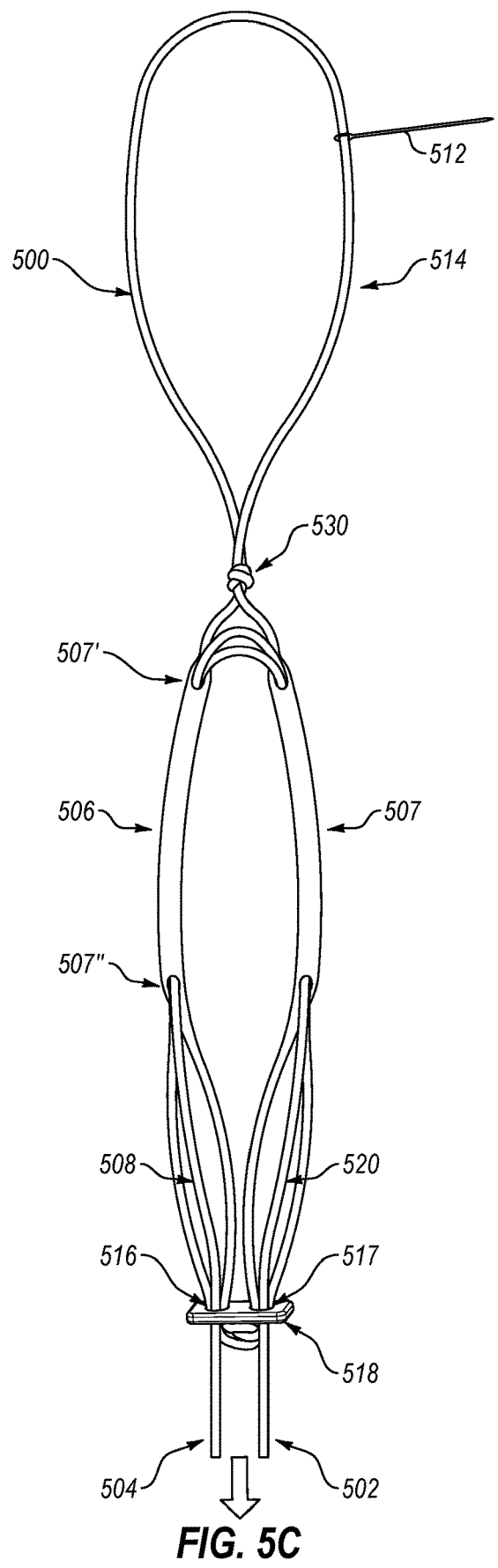

FIG. 5C shows an embodiment that gives the option of pulling the free ends 502, 504 in a different direction compared to FIGS. 5A and 5B. Here, the suture implant is formed as described in connection with FIG. 5B. Then, the first free end 502 is passed through the second buttonhole 517 of the button 518. Then, the second free end 504 is passed through the first buttonhole 516 of the button 518. Now, both the first free end 502 and second free end 504 are extending from the first and second button holes 516, 517, respectively. This allows both the first free end 502 and second free end 504 to be gripped in a single hand to pull in the direction of the arrow to perform the cinching.

Figure 8:
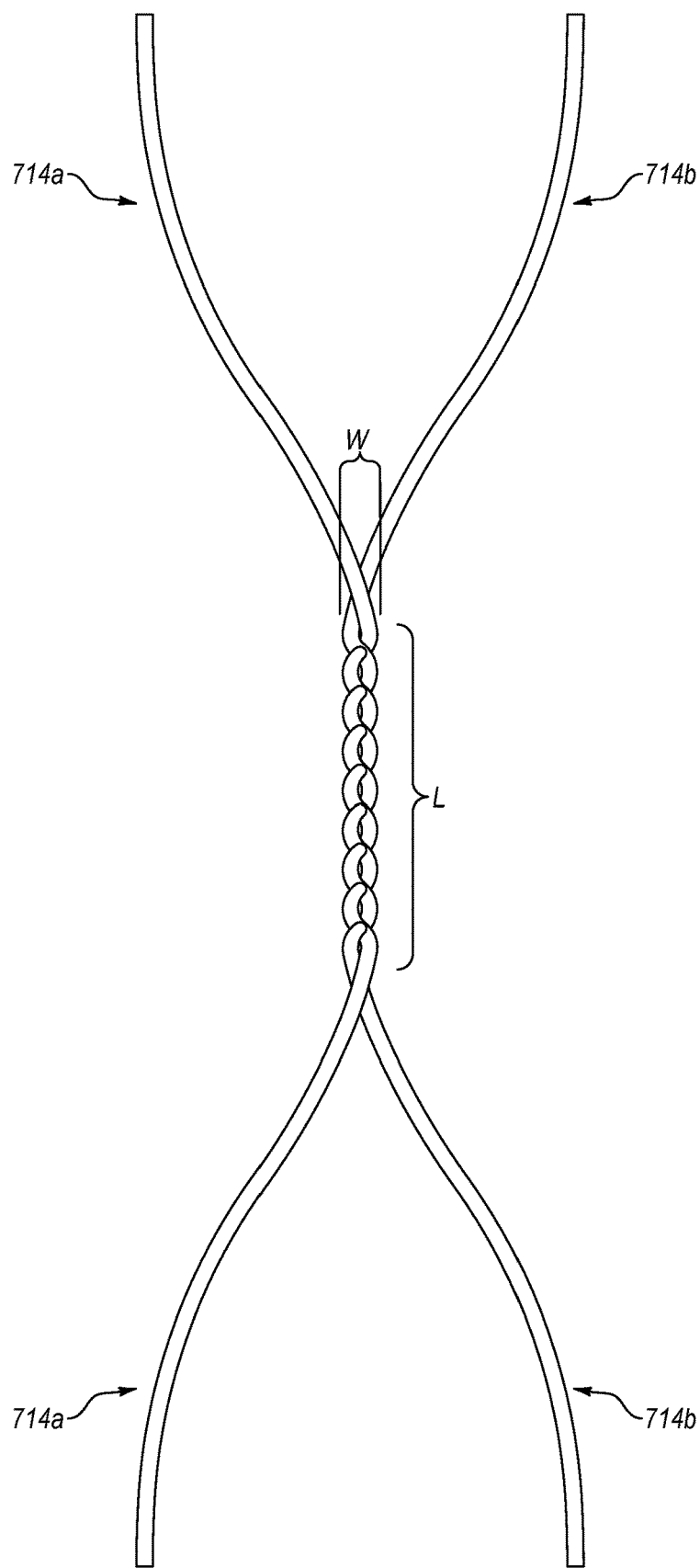
FIG. 8 shows an embodiment of a woven portion for use in any of the embodiments of suture implants illustrated and described herein.

In FIGS. 5A-5C, the knot 530 can be formed by tying the suture cord 500 by making a FIG. 8 shape as shown. However, any manner of tying that is appropriate can be used to form the knot 530 from the suture cord 500. Also, the knot 530 may be a separate member, such as anchor, button, clip, or the like.

Also, it should be recognized that the cord, loop, and button configuration of FIG. 3 can be applied to the embodiments of suture implants of FIGS. 4 and 5A-5C.

Figure 6:
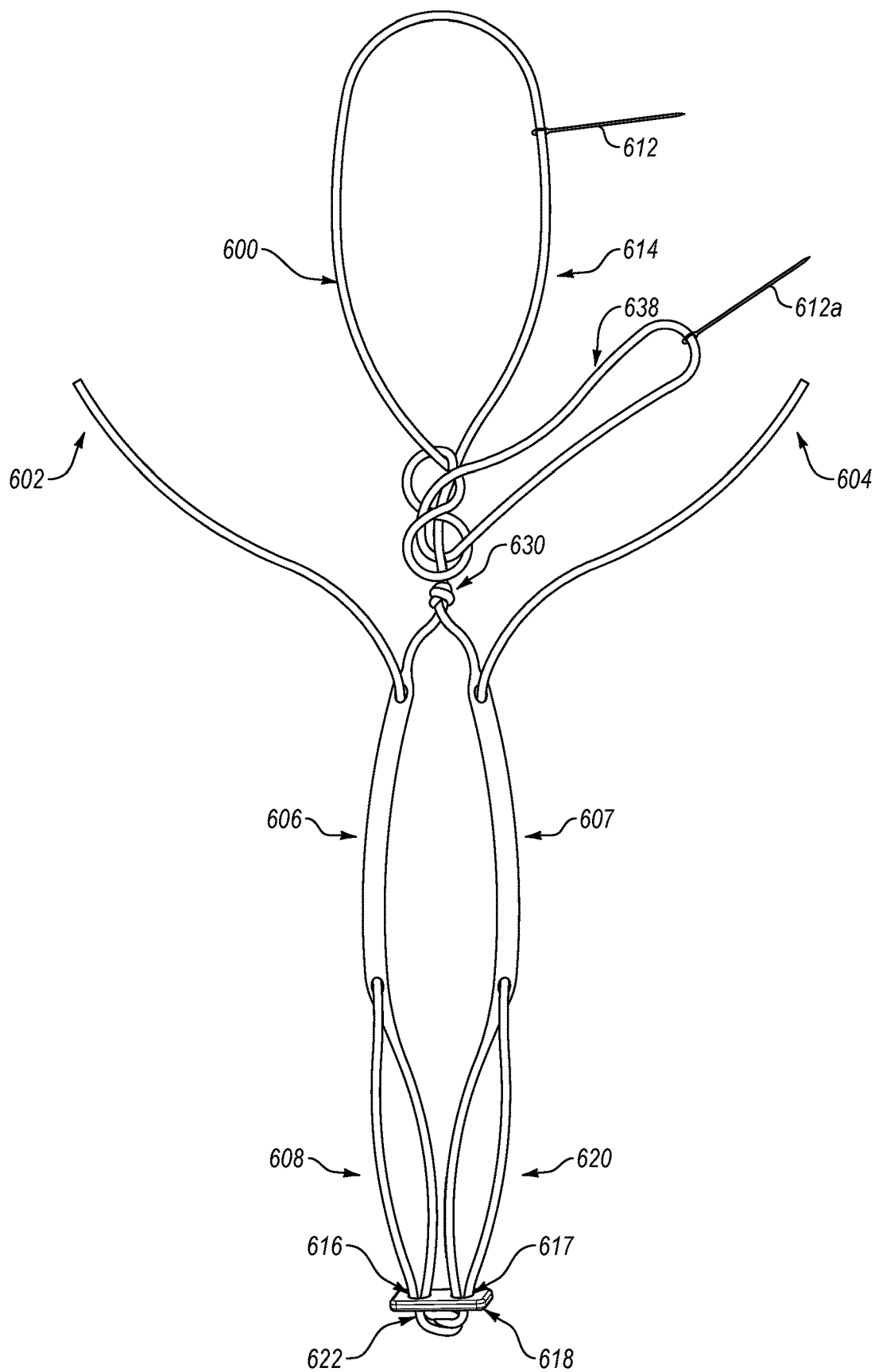
FIG. 6 shows an alternate embodiment of a suture implant.

FIG. 6 shows a suture implant that can be prepared with a suture cord 600 substantially as shown in FIG. 5A. Here, the adjustable first loop 608 is formed by passing the first free end 602 through a portion of the suture cord 600 so that the first splice 606 is formed as shown. The second free end 604 is used to form a second splice 607 by passing the second free end 604 through a portion of the suture cord 600 so that the second splice 607 is formed. However, before formation of the second splice 607, the first loop 608 is passed through a first buttonhole 616 of a button 618 so that a first loop portion of the first loop 608 protrudes from the first buttonhole 616, and then the second free end 604 is passed through a second buttonhole 617 of the button 618 then through and around the first loop 608 to form an interconnection and then back through the second buttonhole 617 of the button 618 and then through the portion of the suture cord 600 to form the second splice 607. Now, there are two splices 606 and 607 as per FIG. 6. Here, instead of the needled loop 614 being a large loop, a knot 630 is formed as shown to be between the first splice 606 and second splice 607. The knot 630 can be formed by tying the suture cord 600 to itself to form the needled loop 614 as well as the adjustable interconnected double loop 622. Here, the adjustable interconnected double loop 622 includes the first loop 608 and third loop 620 as well as the two splices 606, 607 up to the knot 630. The knot 630 is adapted by placing a rebar stitch 638 with a second suture cord 638. The rebar stitch 638 is formed through the knot 630 with the second suture cord 638. The knot 630 with the rebar stitch 638 allows for better coupling with the first tissue. Now, the knot 630 with the rebar stitch 638 can be placed against the first tissue as shown in FIG. 2A, and then the needled loop 614 can be stitched through the rebar stitch 638 and first tissue. The rebar stitch 638 gives more strength to the knot 630. So, the needle 612 is actually passed through the rebar stitch 638 and then through the first tissue multiple times to strongly fasten the knot 630 to the first tissue through the rebar stitch and stitching with the needled loop 614. This keeps the knot 630 from pulling through the first tissue. Also, the free ends 602, 604 may be adapted and placed as shown in FIG. 5B or 5C, or may have knots on the free ends as in FIG. 1E, or be coupled to the button 318 as shown in FIG. 3.

However, the rebar stitch 636 may be an anchor, clip, tie, or other feature formed from another member, which links to the suture cord 500 at the knot 630. The member can be a material that can receive a needle therethrough so that it can be stitched to the first tissue. The material of the member can be a fabric, biodegradable gauze, or the like that can receive stitching through it as described herein.

Figure 7:
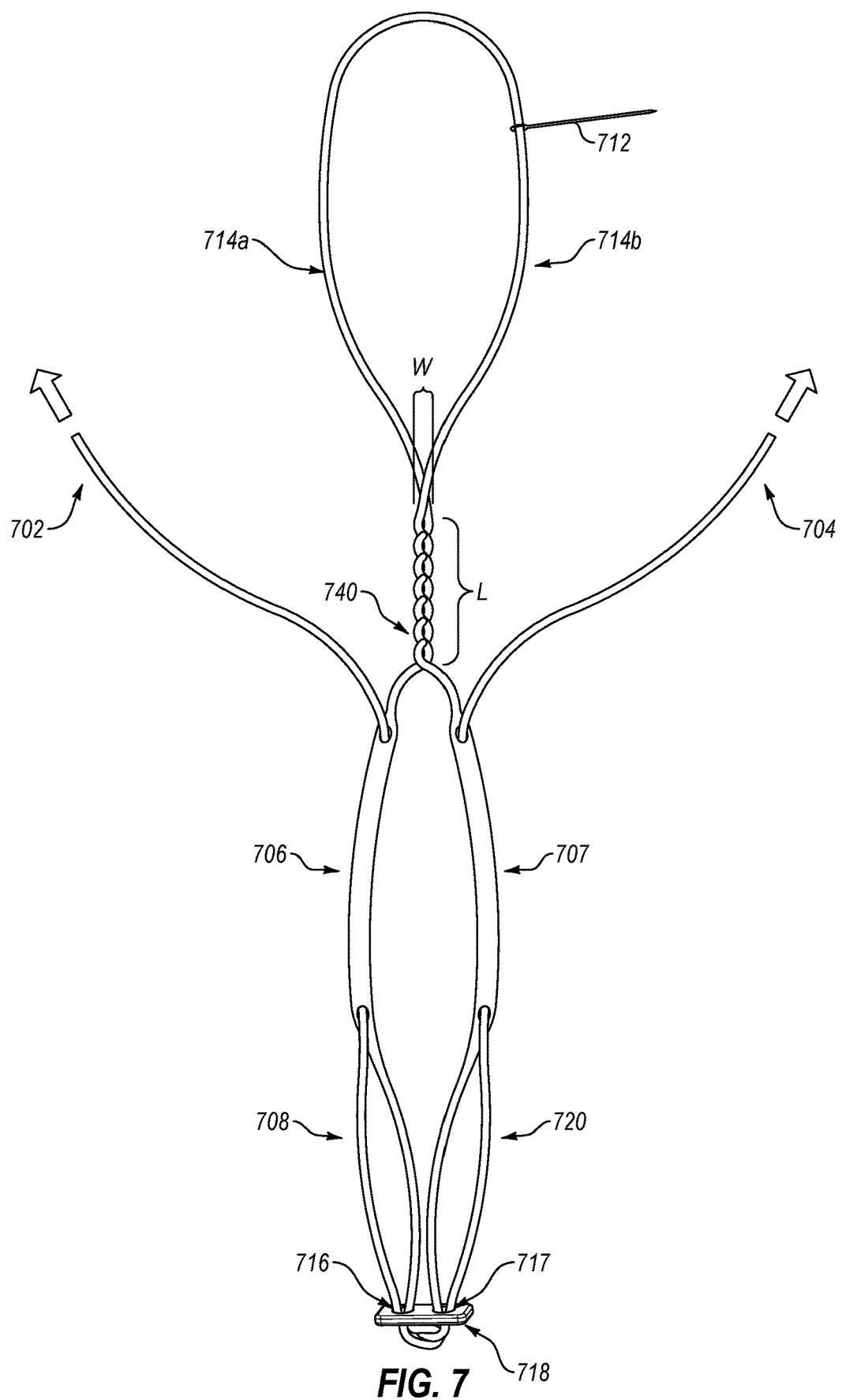
FIG. 7 shows an alternate embodiment of a suture implant.

FIG. 7 shows a suture implant that can be prepared with a suture cord 700 substantially as shown in FIGS. 5A and 6. Here, the adjustable first loop 708 is formed by passing the first free end 702 through a portion of the suture cord 700 so that the first splice 706 is formed as shown. The second free end 704 is used to form a second splice 707 by passing the second free end 704 through a portion of the suture cord 700 so that the second splice 707 is formed. However, before formation of the second splice 707, the first loop 708 is passed through a first buttonhole 716 of a button 718 so that a first loop portion of the first loop 708 protrudes from the first buttonhole 716, and then the second free end 704 is passed through a second buttonhole 717 of the button 718 then through and around the first loop 708 to form interconnection and then back through the second buttonhole 717 of the button 718 and then through the portion of the suture cord 700 to form the second splice 707. Now, there are two splices 706 and 707 as per FIG. 7. When this embodiment of the suture implant is formed with a single suture cord, the needled loop 714 is cut into two strands, 714a and 714b. In fact, the initial steps can be performed without a needle 712 on the needled loop 714. Once the first strand 714a and second strand 714b are available, first strand 714a protrudes from the first splice 706 and the second strand 714b protrudes from the second splice 707. Then, a needle (e.g., 712) is placed on one of strands 714a, 714b and then the needle is inserted through the other of strands 714a, 714b and pulled therethrough, which is alternated with both strands 714a, 714b to form a woven portion 740. FIG. 8 also shows the formation of the woven portion from two separate strands. While the initial pass through may have the needle on either strand 714a or 714b and then inserted through the other, this example will be described with the needle on strand 714a inserted through strand 714b; however, the method could be performed with the needle on strand 714b inserted through strand 714a. In fact, each strand 714a, 714b may have a needle. The first strand 714a is passed perpendicularly through the second strand 714b near the first end of both splices 706, 707, then the second strand 714b is passed perpendicularly through the first strand 714a, then the first strand 714a through the second strand 714b, then the second strand 714b through the first strand 714a in order to prepare a woven portion 740. This process occurs until the woven portion 740 has a sufficient dimension for its width W and/or length L. However, it should also be recognized that other weaving techniques, braiding techniques, or the like may be used to form the woven portion 740. Once a sufficient woven portion 740 is formed, the first strand 714a and second strand 714b can be linked together and/or with the needle 712 to form the needled loop 714 as shown in FIG. 7. For example, the first strand 714a and second strand 714b can be tied together to form a knot (not shown) or both can be tied to the eyelet of the needle 712.

Also, for the embodiment of the suture implant in FIG. 7 the free ends 702, 704 may be adapted and placed as shown in FIG. 5B or 5C, or may have knots on the free ends as in FIG. 1E, or be coupled to the member 718 as shown in FIG. 3.

In one embodiment, the suture implant may be formed from two different cords so that one cord forms one side having the first loop 708 and first splice 706 with the first free end 702. The other cord forms the other side having the second loop 720 with second splice 707 with the second free end 704. Then, the woven portion 740 is formed with the ends opposite of the first free end 702 and second free end 704. Then the needled loop 714 having the needle 712 is formed, such as by tying the opposite ends (e.g., ends of strands 714a, 714b) together.

FIG. 8 shows an enlargement of the woven portion 740 of FIG. 7. Here, the woven structure of the woven portion 740 can be seen. This woven portion 740 is formed by stitching the first strand 714a and second strand 714b together, in alternating stitching pattern. However, the woven portion 740 may be formed by other methods, and may include additional suture cords or suture cord portions. That is, the woven portion 740 may be formed from a single cord (e.g., when cut as per FIG. 7) or from two cords (e.g., as per FIG. 8) or from three cords, four cords, or more. The additional cords can be included by being included in the stitch pattern or by weaving. The result is a woven portion 740 that has a width W and a length L that allows the woven portion 740 to be stitched to the first tissue.

Figure 9B:
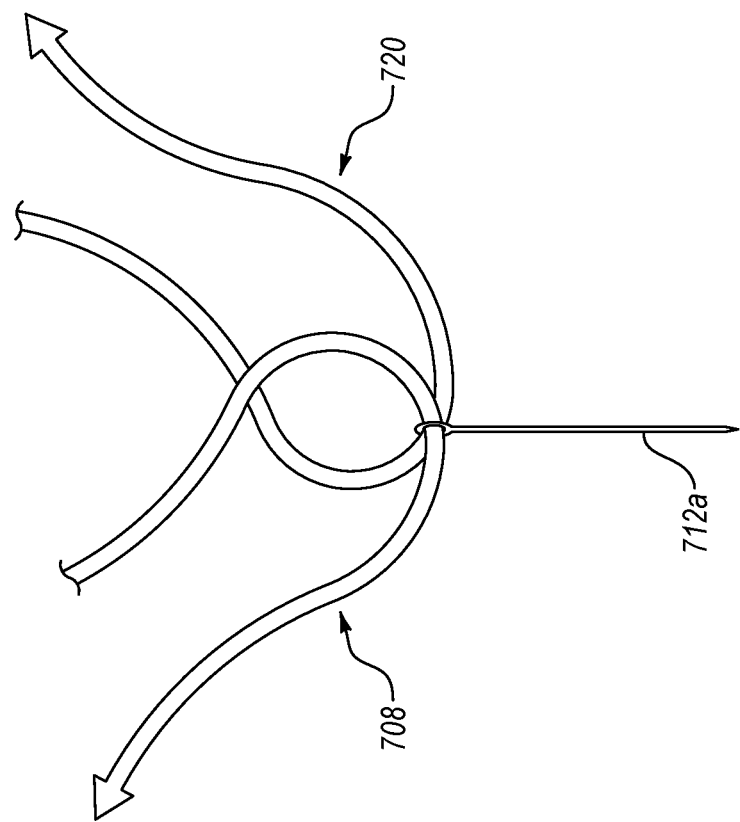
FIGS. 9A and 9B show alternative embodiments of suture implants.
Figure 9A:
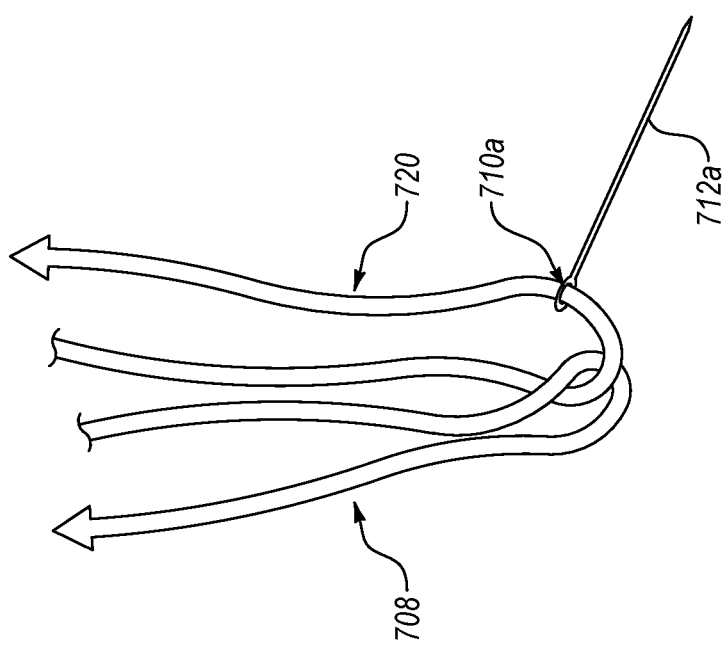

FIG. 9A shows a suture implant substantially as in FIG. 7; however, the button 718 is omitted. Here, the first free end and second free end are looped around each other instead of using the button 718. While the third loop 720 is shown to be passed through the eyelet 710a of a needle 712a, it may be the first loop 708 that is passed through the eyelet 710a of the needle 712a. FIG. 9B is similar to 9A; however, both the first loop 708 and third loop 720 pass through the eyelet 710a of the needle 712a. As such, it should be recognized that the two-holed button of the figures may be replaced with a one-holed member of any kind, such as a bone anchor or needle. Also, the needle 712a may be omitted from the embodiment of FIG. 9A. However, a needle with two eyelets may be used similar to how the two-holed button is used. Accordingly, this allows different features of the different embodiments to be used together, such as those features that are interchangeable with other features. The intercoupling of the first loop 708 and third loop 720 of FIG. 9A or 9B may be applied to any of the other embodiments of the other figures.

The suture implants that are shown in FIGS. 3, 4, 5A, 5B, 5C, 6, 7, and 9 may be used substantially as shown in FIGS. 2A-2D. While the embodiments of these figures may have different configurations, the method of implantation and cinching a first tissue T1 to a second tissue T2 can be performed as shown in FIGS. 2A-2D. In one aspect, the embodiment shown in FIG. 6 can have the knot and rebar stitch stitched to the first tissue. In one aspect, the woven portion of FIGS. 7 and 8 may be stitched to the first tissue, where multi-stitching can be employed. For example, the woven portion may be whip-stitched to the first tissue. As such, the knot and rebar stitch or the woven portion provides a thicker feature that can receive a needle therethrough to make a better and stronger coupling between the suture implant and first tissue.

FIGS. 10A-10B show an embodiment of a suture protector 800 that includes a tube 802 and a cap 804 that couple together to protect a suture implant of any of the embodiments described herein. Here, the suture implant 801 is received through the tube 802 such that a bottom portion having the button and adjustable loops is in the cap 804 with the needed loop 814 having the needle 812 extending from the tube 802. As shown, tube 802 has a bottom end 806 and top end 808, where at the top end 808 a divider 810 is formed. The divider 810 is elongate and coupled at one end to the top end 808 of the tube 802. The divider 810 can rotate (e.g., bend) down to contact or press against the opposite side of the top end 808, such as it does in FIG. 10A. While not shown, the top end 808 can include a recess or divot that receives the free end 811 of the divider 810, such as in a snap fit. This keeps the divider 810 locked down during use until the suture implant 801 is withdrawn therefrom. The free end 811 of the divider 810 can be released to remove the rest of the suture implant 801 from the tube 802. The cap 804 can be received onto the bottom end 806 of the tube 802 and have an internal cavity that retains the rest of the suture implant 801.

As shown in FIG. 10A, the suture implant 801 includes the button (if present), first loop, third loop, interconnected double loop (e.g., formed from interconnected first loop and third loop, first splice, second splice (if present), first free end, second free end, optional knot, optional knot with rebar stitch, optional woven portion, or other features, such that the needled loop 814 extends from the top end 808 so that the needle 812 is available for stitching to the first tissue. Also, the first cord portion 814a and second cord portion 814b of the needled loop 814 can be separated by the divider 810 so that the first cord portion 814a is on a first side formed by the divider 810 and the second cord portion 814b is on a second side formed by the divider 810. The woven portion, knot, knot with rebar stitch may be in the lumen of the tube 802. Also, depending on the relative lengths, the first splice and optional second splice (e.g., depending on embodiment) may also be in the lumen of the tube 802. In one aspect, the needled loop 814, needle 812, woven portion, knot, knot with rebar stitch may extend from the top end, where the divider is between the two splices (e.g., if having two splices) or between the first loop and third loop so as to bisect the interconnected double loop. Various other configurations may be used for the suture protector 800 to produce the suture implant 801 while being stitched to the first tissue.

During use, the suture protector 800 can retain the suture implant 801 as shown in FIG. 10A. The exposed needled loop 814 and needle 812 are used to multi-stitch the first tissue as described herein. Optionally, the woven portion, knot, or knot having rebar stitch can be withdrawn from the tube 802 in order to be multi-stitched to the first tissue, or they can be exposed as provided for stitching to the first tissue. After the suture implant 801 is stitched to the first tissue, the cap 804 can be withdrawn from the bottom end 806 of the tube 802, and the suture implant 801 can be withdrawn from the top end 808 of the tube. Once the suture implant 801 is fully withdrawn from the suture protector 800, the button of the adjustable double loop may be coupled to the second tissue so that the first and second tissues can be cinched together as described herein.

Figure 11A:
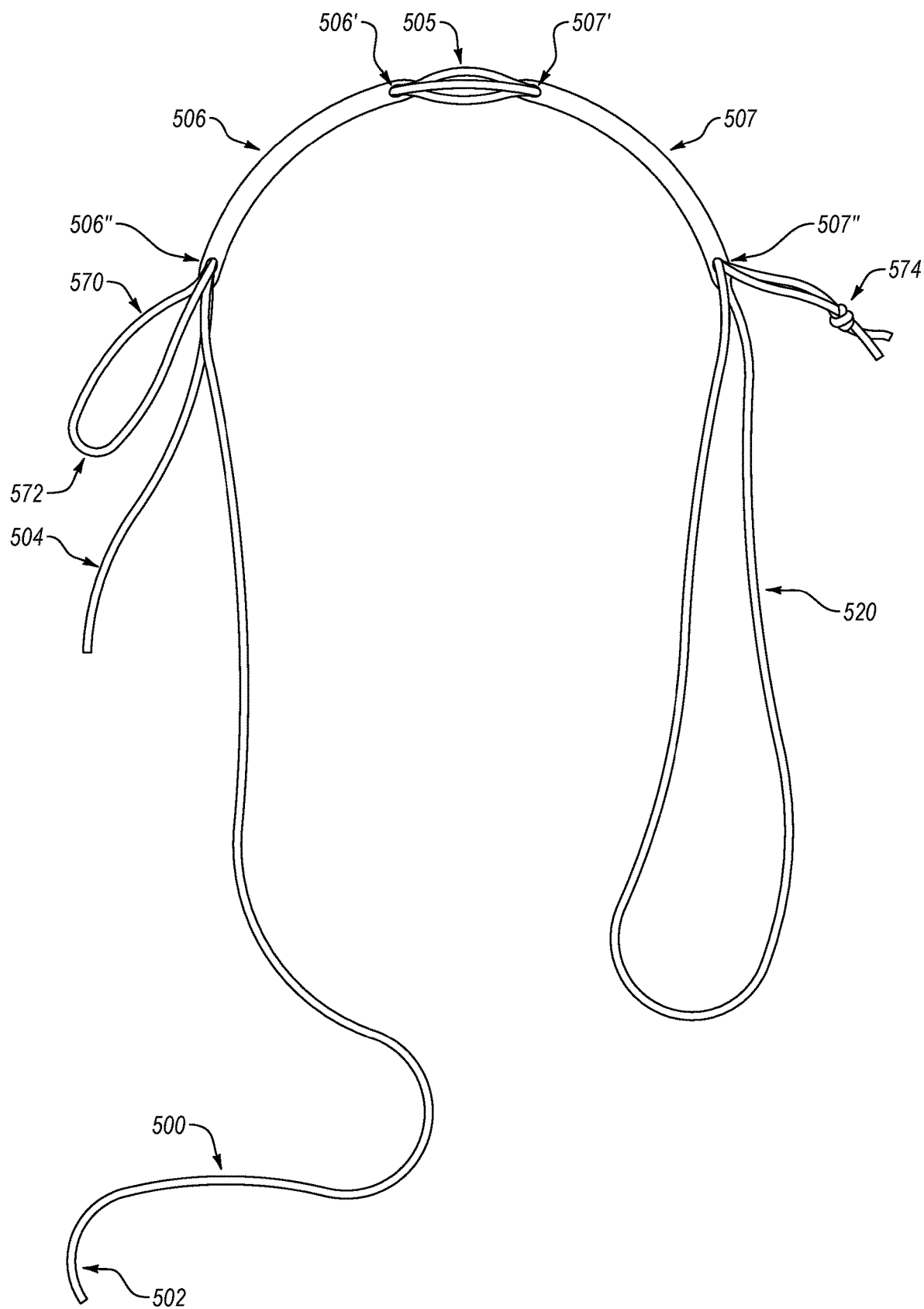
FIGS. 11A-11E show embodiments of suture implants and the method steps for forming the same.

FIG. 11A shows an embodiment of a suture implant that can be formed with a suture cord 500 similar to as shown in FIGS. 5A-5C. Here, the features are formed in a different protocol that described before. This protocol can be used for forming any of the implants here. Here, the adjustable second loop 520 is formed by passing the second free end 504 through a portion of the suture cord 500 so that the second splice 507 is formed as shown and there is a gap 505 and then the second free end 504 is passed through another portion of the suture cord so that the first splice 506 is formed as shown, which leaves the gap 505 between the first splice 506 and second splice 507. Either before or after forming the first splice 506 and second splice 507 with the second free end 504, a shuttle loop 570 is passed through the suture cord 500 to either form the first splice 506 and second splice 507, or passed through the first splice 506 and second splice 507 so that the shuttle loop 570 has a loop portion 572 extending from the first splice second end 506" and a knot portion 574 extending from the second splice second end 507". The adjustable second loop 520 may or may not include a needle 512 thereon.

Figure 11B:
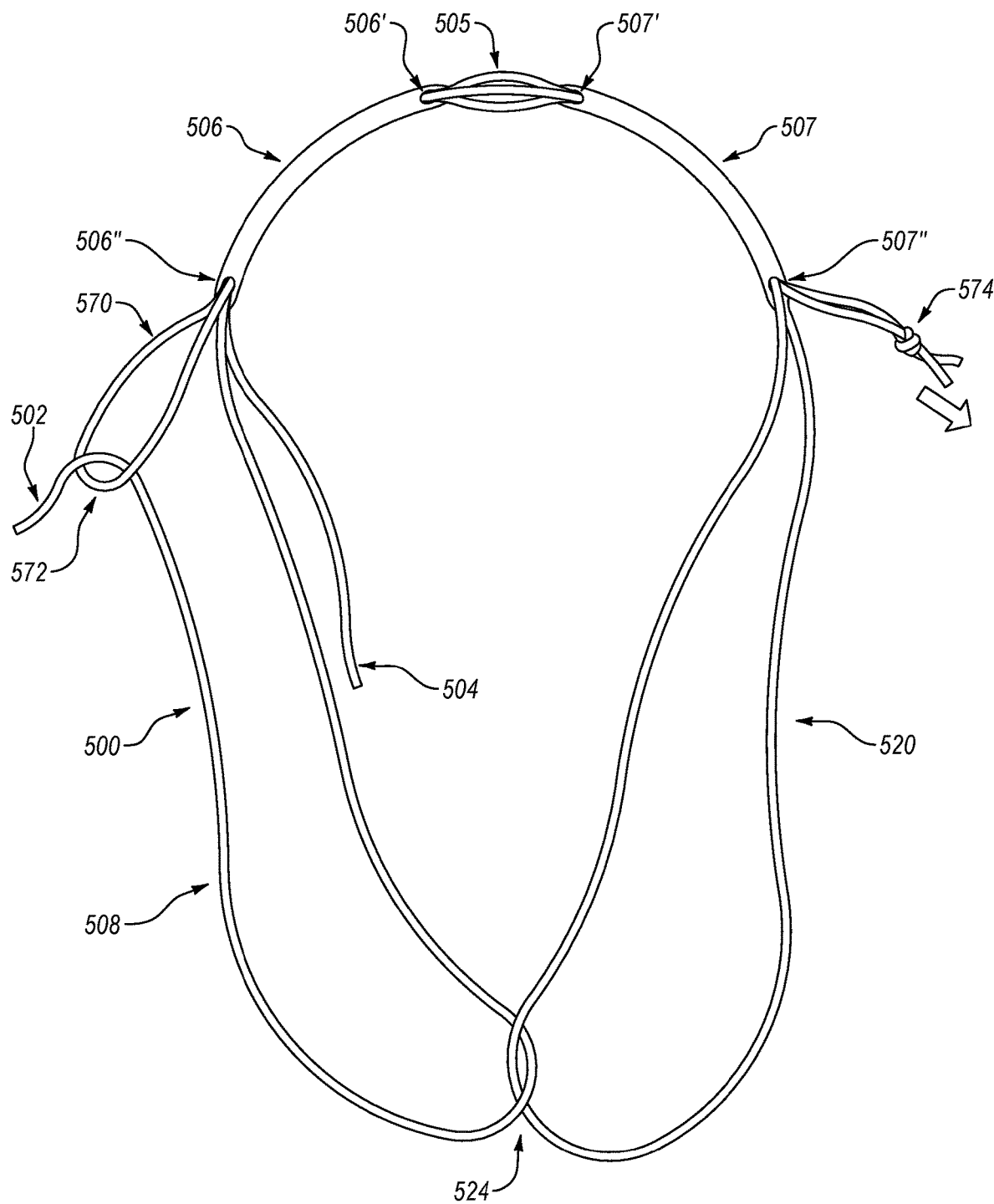

FIG. 11B shows the next step in forming the suture implant after FIG. 11A. Now, the first free end 502 is passed through the adjustable second loop 520 to form the interconnection 524, and then passed through the loop portion 572 of the shuttle loop 570. This is a step in the process of forming the adjustable first loop 508. By looping the first free end 502 through the loop portion 572 of the shuttle loop 570, the shuttle loop 570 can be pulled at the knot portion 574 in the direction of the arrow to pull the first free end 502 through both the first splice 506 and then the second splice 507. This process arrives at the suture implant shown in FIG. 11C, which is similar to as shown in FIG. 5B without the needled third loop 514. Here, the cord in the gap 505 that is not from the first free end 502 or the second free end 504 can be adapted to form the needled third loop 514 or other features.

Figure 11C:
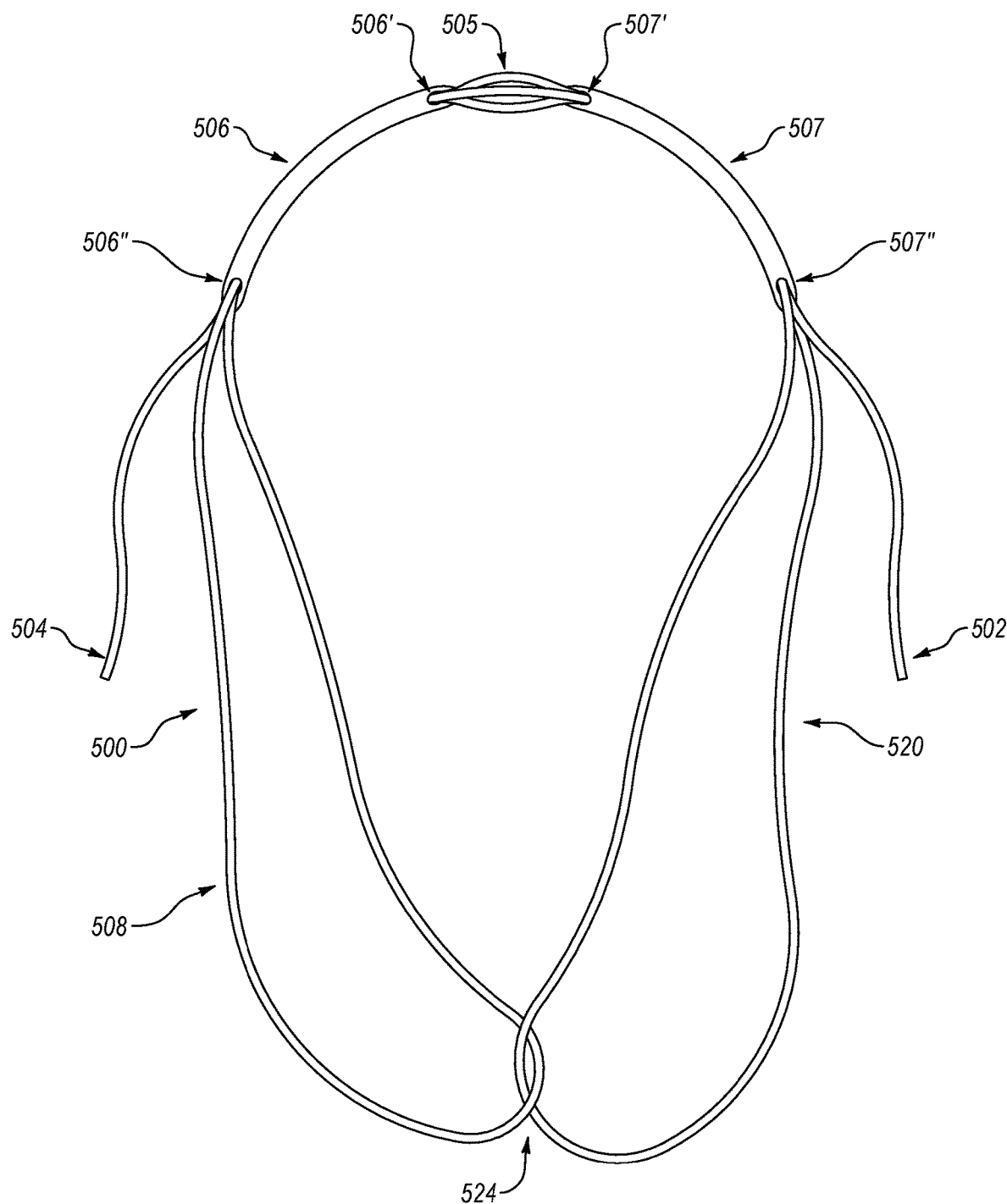
Figure 11D:
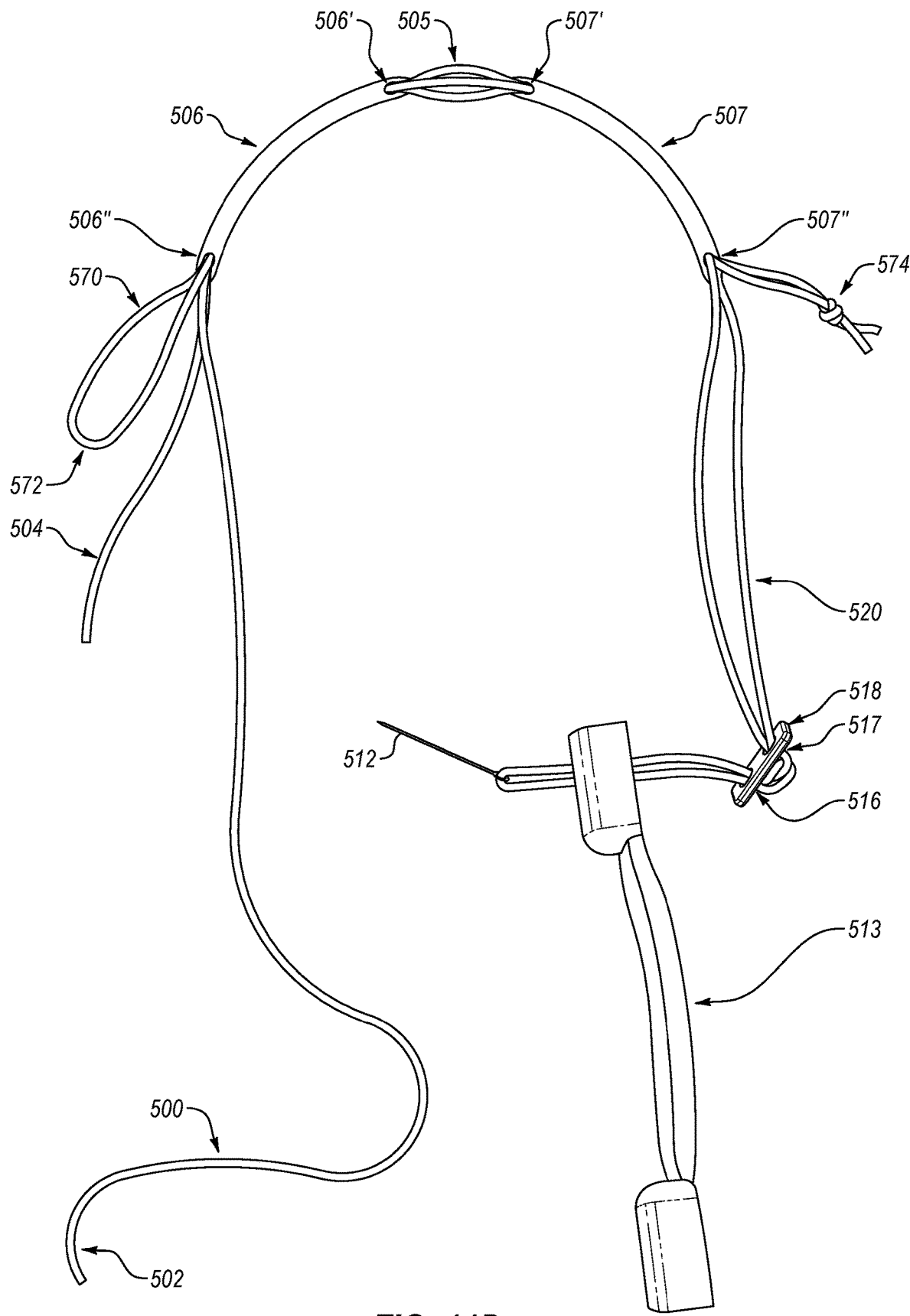
Figure 11E:
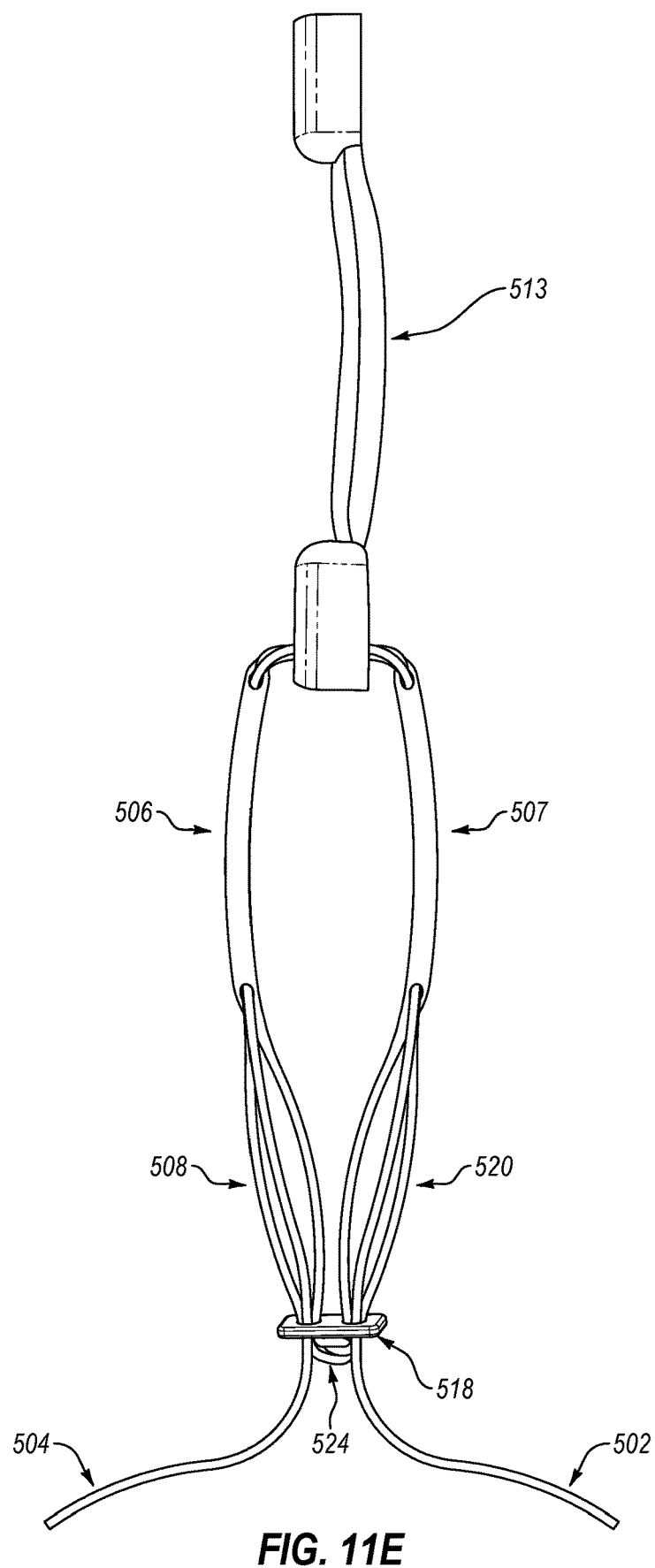

FIG. 11D is an alternative to FIG. 11A. Here, there the adjustable second loop 520 is passed through the second button hole 517 of the button 518 and then through the first button hole 516 of the button 518. A needle 512 is placed on the adjustable second loop 520 before or after passing through the button 518, which results in the needle 512 as shown. The needle 512 is then passed through a graft 513 or other feature. Then, the first free end 502 is passed through the adjustable second loop 520 and then the loop portion 572 of the shuttle loop 570 as described in connection with FIG. 11B, and then the shuttle loop 570 is pulled through the first splice 506 and then second splice 507. Then the graft 513 or other feature is slid along the first adjustable loop 508 and over the second free end 504 and first splice 506 so that it is positioned at the gap 505 to form the suture implant as shown in FIG. 11E. This allows the graft 513 to then be attached to the first tissue as described herein. However, the protocol to arrive at the suture implant of FIG. 11E can include placing the graft 513 at the gap 505 before or after formation of the first splice 506 and second splice 507. Also, the graft 513 can be placed at the gap 505 before the adjustable second loop 520 is passed through the button 518. There are various modifications to the general protocols described herein to arrive at the suture implant of FIG. 11E. Also, it should be recognized that the graft 513 can be any tissue graft, implant, needle, bone anchor, or the like, such as any of the members described herein.

Figure 12:
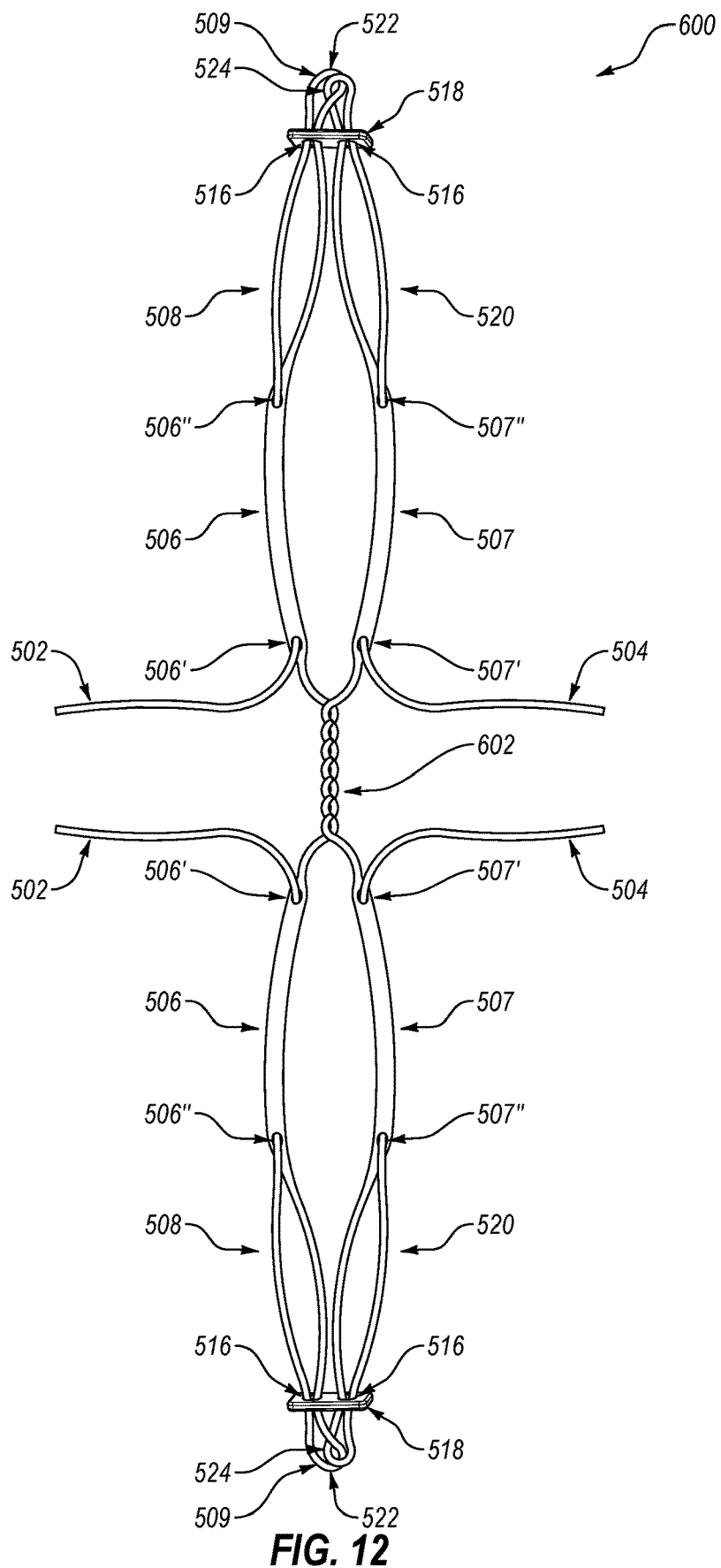
FIG. 12 shows another embodiment of a suture implant.

FIG. 12 shows another embodiment of a suture implant 600. Here, the suture implant 600 is formed generally as described herein. Now, the cinching mechanism is formed at both ends. As such, the same protocols described herein are used for one end and then used for the other end. One way to do this is to cut the needled second loop and then form the same features with the free ends formed by the cutting. A member 602, such as a tape, weave, knot, or other feature is formed to separate the two different cinching mechanisms. As such, the illustrated suture implant 600 is formed.

As before, for the suture implant embodiments of FIGS. 11A-11E and 12 can have the features of FIG. 3 with regard to the buttons instead of as illustrated. Such as change is well within this disclosure. Also, these embodiments may also be formed so that the first free end and second free end can be extended from the first splice and second splice, respectively, as shown in FIG. 5A, or as in FIG. 5B, or as in FIG. 5C. Similarly, the cinching mechanism with the button of FIGS. 5A-5C may be applied to the embodiments of FIGS. 11A-11E and 12. Also, the cinching mechanism may be formulated as in FIGS. 9A-9B for the embodiments in FIGS. 11A-11E and 12. Also, the suture protector of FIGS. 10A-10B may be applied to FIGS. 11A-11E and 12.

It should be recognized that the suture implant embodiments of FIGS. 11C, 11E and 12 can be used to cinch a first tissue T1 to a second tissue T2 as described in connection with FIGS. 2A-2E. The cinching is performed by pulling the first free end 502 and second free end 504. However, there may be slight variances.

In FIG. 11C, the cord that is not attached to the first free end and or second free end can be attached to a member (e.g., any member that can be attached to a tissue, such as those described herein, such as a needle, button, bone anchor another implant, tissue graft, or the like) and then attached to the first tissue T1. The cinching mechanism similarly can be attached to the second tissue, such as with a member (e.g., any member that can be attached to a tissue, such as those described herein, such as a needle, button, bone anchor another implant, tissue graft, or the like). In FIG. 11E, the graft 513 may be attached to a tissue as is known in the art. In one example, the graft 513 is stitched (e.g., multi-stich, which stich) to the first tissue T1, and then the member 518 is attached to the second tissue T2 and then the cinching is performed by pulling the first free end 502 and second free end 504. In FIG. 12, each member 518 can be attached to a tissue, one to the first tissue T1 and one to the second tissue T2, and then the cinching of both ends can be performed by pulling both first free ends 502 and both free ends 504.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In one embodiment, a method of making a suture implant is provided. The method can include providing a suture cord having a first free end and opposite second free end. A splice is formed on the suture cord, where the splice has a splice first end and an opposite splice second end. A first loop is formed by having the first free end pass into the splice first end, through the splice, and out from the splice second end. Alternatively, the first loop can be formed by passing the second free end into the splice second end, through the splice, and out from the splice first end. In either process for forming the first loop, both the first free end and second free end extend from the splice first end and the first loop extends from the splice second end. A needle is placed onto the suture cord by the second free end passing through an eyelet of the needle. A second loop opposite of the first loop with the splice therebetween is formed by the second free end passing back through the splice by being inserted into the splice first end, through the splice, and out from the splice second end such that the needle is on the second loop. Now, the first loop and second free end extend from the splice second end. A member, such as a bone anchor or button, having two apertures is provided. The first loop is passed through a first aperture from a first side of the member to extend from a second side of the member. The second free end is passed through the second aperture from the first side of the member to extend from the second side of the member, passed through the portion of the first loop extending from the first aperture that is extending from the second side of the member and looped around the first loop and then passed back through the second aperture from the second side of the member to extend from the first side of the member. This allows the second end to form a loop extending from the second side of the member that is intertwined with the portion of the first loop that extends from the second side of the member. The second free end is then passed through the splice by inserting into the splice second end, through the splice and out from the splice first end so that now the second free end extends from the splice first and along with the first free end and the first loop. Once the second free end passes through the splice in this step, a third loop is formed that intertwines with the first loop, where both the first loop and third loop extend from the splice second end and intertwine at the second side of the member. Together, the first loop and third loop form an interlocked loop around the member.

In one option, no member is provided. In this instance, a second loop opposite of the first loop with the splice therebetween is formed by the second free end passing back through the splice by being inserted into the splice first end, through the splice, and out from the splice second end such that the needle is on the second loop. Now, the first loop and second free end extend from the splice second end. Without the member, the second free end is passed through the first loop so as to intertwine with the first loop and then the second free end is passed back through the splice by being passed into the splice second end, through the splice and back out the splice first end so as to form a third loop that interlocks with the first loop. Now, both the first loop and third loop extend from the splice second end and intertwine. Together the first loop and third loop form an interlocked loop extending from the splice second end. Pulling on the first free end (e.g., from the splice first end) cinches the first loop and thereby cinches the interlocked loop. Pulling on the second free end (e.g., from the splice first end) cinches the third loop and thereby cinches the interlocked loop.

Accordingly, the first loop is a cinchable loop by pulling on the first free end and the third loop is a cinchable loop by pulling on the second free end, and thereby the interlocked loop is cinchable by pulling on the first free end and/or the second free end.

In one embodiment, a knot or other anchoring feature is formed at the splice first end where the first free end, second free end, and second loop extend therefrom. The knot or other anchoring feature can be on the slice and/or second loop so that the second loop has a fixed dimension or so that the second loop does not cinch when the first free end or second free end is pulled.

In one embodiment, the methods for making the suture implant as described herein can result in a usable suture implant. Accordingly, a suture implant comprising one or more suture cords can be formed to include the following features. While more than one cord can be used, it can be advantageous to form the implant from a single cord. However, the splice may be a separate tube member or it can be formed from the cord being fashioned into a splice by having a portion of the cord passed through itself to form the splice. The implant can include a suture cord having a splice so that a first free end extends from a splice first end and second free end extends from the splice first end. A first loop extends from a splice second end, wherein the first loop is adjustably coupled to the first free end. A second loop extends from the splice first end, and where a needle is slidable on the second loop. A third loop extends from the splice second end, where the third loop is adjustably coupled to the second free end. The first loop and second loop both extend from the splice second end and are intertwined so as to be interconnected to form an interconnected loop that is adjustable by cinching the first loop by pulling the first free end and/or cinching the third loop by pulling the second free end. Optionally, the first loop and third loop pass through different apertures of a member and interlock on a side of the member opposite of the splice second end. In one aspect a knot or anchor is formed on the second loop so that the second loop is inhibited from shortening or cinching or otherwise being pulled into the splice. In one aspect, the knot or anchor on the second loop may also be on the splice to inhibit the second loop from passing into or through the splice or otherwise cinching. In one aspect, either or both the first free end and/or second free ends can have a knot or anchor thereon so that the first free end and/or second free end does not pass through the splice first end and into or through the splice. In one aspect, the suture implant is formed from a single suture cord, such as via the methods described herein. However, each component described herein can be a separate suture cord if desired. In one aspect, the splice is a tubular member, either a tube formed into the suture cord or a separate tubular member located around the suture cord. When included, the member with the two apertures that receive the first loop or second loop is a button, suture, screw, plate, bone anchor, or any implant of any type, such as any orthopedic device.

In one embodiment, the member having the two apertures includes a body, button, anchor, or second implant having at least two spaced apart holes each being dimensioned to receive the cord of the first loop and second loop therethrough.

In one embodiment, the first free end and/or second free end are ends of tensioning strands that can be tensioned to cinch the first loop and/or third loop and/or interlocked loop that is formed from the first loop and third loop. In one aspect, the tensioning strands having the first and second free ends each has an anchor member that inhibits a free end of one of the tensioning strands from being pulled through the splice.

In one embodiment, a method of cinching a first tissue to a second tissue can be performed with the suture implant as described in any of the embodiments herein. The cinching method can include providing a suture implant in accordance with one of the embodiments described herein or illustrated in the figures. The cinching method can include multi-stitching the suture implant into the first tissue, such as with a whipstitch, where the second loop having the needle thereon is multi-stitched to the first tissue. Then, the second loop is cut to form two strands. The needle is removed from the suture implant by being withdrawn from one of the two strands (e.g., from the strand having the needle). Then, the two strands that were formed from cutting the second loop are tied together or otherwise fastened together and to the first tissue so that the suture implant is affixed to the first tissue. This can include tying the two strands into a knot to affix the suture implant to the first tissue. When the suture implant includes the member having the interlocked loop, the member (e.g., button or anchor or the like) is attached to the second tissue. Then, an act of pulling one or both of the first and second free ends is performed to cinch the first tissue toward the member, and thereby the splice and the first tissue are cinched to (e.g., optionally into) the second tissue. In one aspect, both of the first and third loops, and thereby the interconnected loop also cinch down by pulling the first and second free ends. In one aspect, the first and second free ends can be pulled independently or simultaneously, or one pulled, and then the other pulled, and repeated in an alternating format, or combination thereof. Once the first tissue and second tissue are sufficiently cinched together, the cords of the first and second free ends can be cut and optionally knotted to leave the suture implant linking the first tissue to the second tissue.

In one embodiment, a method of making a suture implant can be performed as described below. The method can include providing a suture cord having a first free end and opposite second free end. The method can include forming a first splice on the suture cord, the first splice having a splice first end and an opposite splice second end. The method can include forming a first adjustable loop by having the first free end pass back through the splice second end of the first splice and out from the splice first end. The method can include passing a second free end through an eyelet of a needle. The method can include passing the first loop through a first buttonhole of a button. The method can include passing the second free end through a second buttonhole of the button, then passing the second free end through the portion of the first loop that extends from the first buttonhole, then passing the second free end back through the second buttonhole of the button so as to form an adjustable intertwined loop, the intertwined loop formed from the first loop and the loop formed by the second free end passing around the first loop and back through the second buttonhole. The method can include forming a second splice on the suture cord by passing the second free end back through a portion of the suture cord. In one aspect, the first free end can be pulled to cinch one side of the adjustable intertwined loop by cinching the adjustable first loop. In one aspect, the second free end can be pulled to cinch the other side of the adjustable intertwined loop compared to when pulling the first free end, where pulling the second free end cinches the adjustable third loop. In one aspect, pulling both the free ends can cinch the adjustable intertwined loop. In one aspect, the loop having the needle is not adjustable. In one aspect, the method can include forming a knot or other anchor on the loop having the needle, such as between the first splice and the second splice. In one aspect, the method can include forming a knot or other anchor that inhibits the loop having the needle from being pulled through the first splice and/or second splice when one or both free ends are pulled. Here, cinching is performed by pulling the first and second free ends toward the first tissue.

In one embodiment, the method can further include passing the first free end through the second splice and passing the second free end through the first splice. Now, the direction of pulling the free ends to cinch is reversed so that the pulling is more toward the second tissue.

In one embodiment, the method can further include passing the first free end through one of the buttonholes and passing the second free end through the other buttonhole. This can be performed after the first free end is through the second splice and the second free end is through the first splice. This changes the direction of pulling to be even more toward the second tissue, and allows cinching by pulling both free ends with one hand.

In one embodiment, a suture implant can include one or more suture cords formed into the structures of the figures. However, it is preferable to use only one suture cord. In some instances, two suture cords can be used, one for each side of the suture implant, and then the two structures can be joined by joining the two suture cords.

In one embodiment, a suture implant can include a suture cord having a first splice so that a first free end extends from the splice first end. A second splice is formed by the second free end passing through the suture cord. A loop (e.g., second loop) having a needle slidable thereon is formed before forming the second splice, the loop extending from the first splice and second splice. A first adjustable loop (e.g., first loop) extends from the first splice and passes through a first buttonhole of a button. A second adjustable loop (e.g., third loop) extending from second splice is formed, which has passed through a second buttonhole of the button. The first and second adjustable loops are intertwined so that the loops are linked such that each passes through the other once to form the intertwined junction and form an intertwined adjustable double loop. The intertwined adjustable double loop is formed before forming the second splice. In one aspect, the button is slidable on the first and second adjustable loops and thereby slidable relative to the intertwined adjustable double loop. In one aspect, a knot or anchor is on the implant that inhibits the loop having the needle from passing into the first splice or second splice. In one aspect, the suture implant is formed by a single suture. In one aspect, the suture implant is formed by more than one suture, such as by two sutures. In one aspect, the splice is a tubular member. In one aspect, the button is a button, suture, screw, plate, bone anchor, or any implant of any type, such as any orthopedic device. In one aspect, the button includes a body, button, anchor, or second implant having at least two spaced apart holes each being dimensioned to receive the cord of the adjustable intertwined loop therethrough. In one aspect, the first free end and second free end are ends of tensioning strands. In one aspect, the tensioning strands having the free ends each has an anchor member that inhibits a free end of one of the tensioning strands from being pulled through the splice. In one aspect, a knot, having a rebar stitch, or woven portion is located between the first and second splices, and between the two splices and the needle on the needled loop. In one aspect, the knot, having a rebar stitch, or woven portion is on the needled loop or at a place thereon adjacent to the splices.

In one embodiment, a method of cinching a first tissue to a second tissue is provided. Such a method can include the following steps. The method can include providing a suture implant in accordance with one of the claims or illustrated in the figures. The method can include multi-stitching the suture implant into the first tissue (e.g., whipstitch). The method can include cutting a loop having a needle to form two strands, removing the needle from the suture implant, and tying the two strands into a knot to affix the suture implant to the first tissue. The method can include attaching the button (e.g., or anchor or the like) to the second tissue.

The method can include pulling one or both of free ends to cinch the first tissue toward the button, and thereby cinch the first tissue to (e.g., optionally into) the second tissue. In one aspect, the adjustable first and third loops also cinch down by pulling both the free ends. In one aspect, pulling both free ends cinches the adjustable intertwined loop. In one aspect, the free ends can be pulled independently or simultaneously, or one pulled, and then the other pulled, and repeated in an alternating format, or combinations thereof. The method can include cutting the cords of the free ends to leave the implant linking the first tissue to the second tissue. Optionally, knots can be formed at the ends of the splices where the free ends are cut, such that the knots inhibit the cut ends to be pulled back through the splices.

In one embodiment, a suture implant can include one or more suture cords having the following: at least one splice; a first free end extending from a first end of the at least one splice; an adjustable first loop extending from a second end of the at least one splice that has the first free end extending from the first end, wherein the first free end is connected to the adjustable first loop; a second free end extending from a first end of the at least one splice; a second loop having a cord portion extending from the first end of the at least one splice that has the first free end extending therefrom and extending from the first end of the at least one splice that has the second free end extending therefrom; optionally, a tissue fastener on the second loop; and an adjustable third loop extending from a second end of the at least one splice that has the second free end extending from the first end, wherein the second free end is connected to the adjustable third loop, wherein the adjustable first loop and adjustable third loop are interconnected and looped around each other. In one aspect, the tissue fastener is selected from a button, anchor, implant, needle, suture, screw, plate, bone anchor, graft, tissue graft, surgical tape, orthopedic device, or combination thereof.

In one embodiment, a suture implant can include: the first free end extending from the first end of a first splice; the adjustable first loop extending from a second end of the first splice, wherein the first free end is connected to the adjustable first loop; the second free end extending from the first end of the first splice; the second loop extending from the first end of the first splice; and the adjustable third loop extending from the second end of the first splice, wherein the second free end is connected to the adjustable third loop, wherein the adjustable first loop and adjustable third loop are interconnected and looped around each other.

In one embodiment, the suture implant can include: the first free end extending from the first end of a first splice; the adjustable first loop extending from a second end of the first splice, wherein the first free end is connected to the adjustable first loop; the second free end extending from the first end of a second splice; the second loop having a cord portion extending from the first end of the first splice and first end of the second splice; and the adjustable third loop extending from the second end of the second splice, wherein the second free end is connected to the adjustable third loop, wherein the adjustable first loop and adjustable third loop are interconnected and looped around each other.

In one embodiment, a method of forming an embodiment of the suture implant that includes two splices can include: providing a single suture cord; forming the second splice and then the first splice by passing the second free end into a lumen of the suture cord and then out from the lumen of the suture cord to form the second splice and then into a lumen of the suture cord and then out from the lumen of the suture cord to form the first splice, which forms an adjustable third loop; providing a shuttle loop having a loop end and knot end; passing the loop end of the shuttle loop through a splice second end of the second splice and out from a splice first end of the second splice and then through a splice first end of the first splice and out from a splice second end of the first splice; passing the first free end through the adjustable third loop; passing the first free end through the loop end of the shuttle loop; and pulling the knot end of the shuttle loop so as to pull the loop end of the shuttle loop and first free end through the first splice and then the second splice, which forms the adjustable first loop and second loop. In one aspect, the method can include forming a gap between the first splice and the second splice. In one aspect, the method can include forming the adjustable third loop to have a needle thereon by passing the second free end through an eyelet of the needle before passing the second free end through the second splice. In one aspect, the method can include passing the needle through a tissue fastener before the first free end is passed through the adjustable third loop. In one aspect, the method can include the tissue fastener being selected from a button, anchor, implant, needle, suture, screw, plate, bone anchor, graft, tissue graft, surgical tape, orthopedic device, or combination thereof. In one aspect, the method can include positioning the tissue fastener between the first splice and second splice. In one aspect, the method can include removing the needle from the adjustable third loop after the adjustable third loop passes through the tissue fastener. In one aspect, the method can include passing the adjustable third loop through a member before the first free end is passed through the adjustable third loop. In one aspect, the method can include the member being selected from a button, anchor, implant, needle, suture, screw, plate, bone anchor, graft, tissue graft, surgical tape, orthopedic device, or combination thereof. In one aspect, the method can include passing the adjustable first loop through the member. In one aspect, the method can include passing the adjustable first loop through the member such that the adjustable first loop is through a first hole of the member and the adjustable third loop is through a second hold of the member, wherein the adjustable first loop and adjustable third loop are interconnected between the first hold and second hold of the member. In one aspect, the method can include passing the second free end through the first hole of the member and passing the first free end through the second hole of the member.

In one embodiment, the suture implant can include a first portion and second portion each having: a first free end extending from a first end of a first splice; an adjustable first loop extending from a second end of the first splice, wherein the first free end is connected to the adjustable first loop; a second free end extending from a first end of a second splice; and the adjustable third loop extending from the second end of the second splice, wherein the second free end is connected to the adjustable third loop, wherein the adjustable first loop and adjustable third loop are interconnected and looped around each other; and a first cord portion extending from the first end of the first splice and a second cord portion extending from first end of the second splice; and the first portion and second portion connected together between the first cord portions and second cord portions. In one aspect, the suture implant can include one or more of the following: a first member coupled to the adjustable first loop and adjustable third loop of the first portion, the first member selected from a surgical tape, graft, tissue graft, button, anchor, implant, needle, suture, screw, plate, bone anchor, orthopedic device, or combination thereof; a second member coupled to the adjustable first loop and adjustable third loop of the second portion, the second member selected from a surgical tape, graft, tissue graft, button, anchor, implant, needle, suture, screw, plate, bone anchor, orthopedic device, or combination thereof; or a third member between the first portion and second portion, the third member being selected from a knot, knot with rebar stitch, surgical tape, graft, tissue graft, button, anchor, implant, needle, suture, screw, plate, bone anchor, orthopedic device, or combination thereof.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety, including: EP20120188229; EP20120177242; EP20120185616; EP20140159454; EP20130172604; U.S. application Ser. No. 13/102,182; U.S. application Ser. No. 11/541,506; U.S. Application Publication No. US20080082128, U.S. Application Publication No. US20140276992.

Specific reference is also made to the following U.S. Provisional Applications, which are incorporated herein by specific reference in their entirety: 62/180,347 filed Jun. 16, 2015; 62/200,458 filed Aug. 3, 2015; 62/212,307 filed Aug. 31, 2015; and 62/253,457 filed Nov. 10, 2015. It is noted that features of the present invention are described in the incorporated provisional applications, and the subject matter thereof forms a basis for the present application. Additionally, the devices and portions of the devices and the methods of use in the Companion Figures can be applied to the inventive device described herein, and wherein such portions of devices and methods of use can be modified to use the device described herein in accordance with the descriptions provided.

The invention claimed is:

1. A suture implant comprising one or more suture cords having:
a stitchable fixation member having a width and length extending between a first end and a second end, wherein the stitchable fixation member is configured to be stitched therethrough to a body, wherein the stitchable fixation member includes a woven and/or braided construct that is formed by one or more suture cords being woven and/or braided together;
an adjustable loop coupled to the first end of the stitchable fixation member by having a first adjustable loop end and second adjustable loop end both extending from the same first end of the stitchable fixation member;
a fastening member having at least one aperture receiving the adjustable loop through the at least one aperture so that the fastening member is slidable relative to the adjustable loop, and the fastening member is configured for being fastened to a tissue or bone; and
a stitching loop coupled to the second end of the stitchable fixation member by having a first stitching loop end and second stitching loop end both extending from the same second end of the stitchable fixation member, and the stitching loop is configured to stitch the stitchable fixation member to the body.

2. The suture implant of claim 1, further comprising a needle attached to the stitching loop, wherein the body is a tissue or graft or medical device that is stitchable.

3. The suture implant of claim 2, wherein the fastening member is selected from a button, anchor, implant, needle, suture, screw, plate, bone anchor, graft, tissue graft, surgical tape, orthopedic device, or combination thereof.

4. The suture implant of claim 3, wherein the at least one aperture of the fastening member has a first aperture receiving the adjustable loop therethrough and a second aperture receiving the adjustable loop therethrough so that the fastening member is slidable relative to the adjustable loop.

5. The suture implant of claim 1, the length is greater than the width.

6. The suture implant of claim 5, wherein the stitchable fixation member is flat.

7. A method of cinching a first tissue to a second tissue, the method comprising:
providing the suture implant of claim 1;
multi-stitching the stitchable fixation member to the first tissue;
attaching the fastening member to the second tissue; and
cinching the first tissue and second tissue together by adjusting the adjustable loop to draw the stitchable fixation member to the fastening member.

8. A suture implant comprising one or more suture cords having:
a stitchable fixation member having a width and length extending between a first end and a second end, wherein the stitchable fixation member is configured to be stitched therethrough to a body;
an adjustable loop coupled to the first end of the stitchable fixation member by having a first adjustable loop end and second adjustable loop end both extending from the same first end of the stitchable fixation member, wherein the adjustable loop includes a first adjustable subloop in a first adjustable loop arm extending from the first adjustable loop end and a second adjustable subloop in a second adjustable loop arm extending from the second adjustable loop end, the first adjustable subloop and second adjustable subloop being connected together to form the adjustable loop;
a fastening member having at least one aperture receiving the adjustable loop through the at least one aperture so that the fastening member is slidable relative to the adjustable loop, and the fastening member is configured for being fastened to a tissue or bone; and
a stitching loop coupled to the second end of the stitchable fixation member by having a first stitching loop end and second stitching loop end both extending from the same second end of the stitchable fixation member, and the stitching loop is configured to stitch the stitchable fixation member to the body.

9. The suture implant of claim 8, wherein:
the first adjustable subloop extends from a first splice on the first adjustable arm; and
the second adjustable subloop extends from a second splice on the second adjustable arm.

10. The suture implant of claim 9, wherein:
a first pullable free end extends from the first adjustable subloop through the first splice so as to extend from the first splice; and
a second pullable free end extends from the second adjustable subloop through the second splice so as to extend from the second splice.

11. A method of cinching a first tissue to a second tissue, the method comprising:
providing the suture implant of claim 10;
multi-stitching the stitchable fixation member to the first tissue;
attaching the fastening member to the second tissue; and
cinching the first tissue and second tissue together by adjusting the adjustable loop to draw the stitchable fixation member to the fastening member, wherein the adjusting of the adjustable loop includes:
pulling the first pullable free end to cinch the first adjustable subloop; and
pulling the second pullable free end to cinch the second adjustable subloop.

12. The suture implant of claim 9, wherein the first adjustable subloop and second adjustable subloop are intertwined.

13. A suture implant comprising one or more suture cords having:
a stitchable fixation member having a width and length extending between a first end and a second end, wherein the stitchable fixation member is configured to be stitched therethrough to a body;
an adjustable loop coupled to the first end of the stitchable fixation member by having a first adjustable loop end and second adjustable loop end both extending from the same first end of the stitchable fixation member;
a fastening member having at least one aperture receiving the adjustable loop through the at least one aperture so that the fastening member is slidable relative to the adjustable loop, and the fastening member is configured for being fastened to a tissue or bone, wherein the at least one aperture of the fastening member has a first aperture receiving two first cord portions of the adjustable loop therethrough and a second aperture receiving two second cord portions of the adjustable loop therethrough so that the fastening member is slidable relative to the adjustable loop; and
a stitching loop coupled to the second end of the stitchable fixation member by having a first stitching loop end and second stitching loop end both extending from the same second end of the stitchable fixation member, and the stitching loop is configured to stitch the stitchable fixation member to the body, wherein the adjustable loop includes a first adjustable subloop and a second adjustable subloop connected to form the adjustable loop, and wherein:

the two first cord portions are of the first adjustable subloop; and the two second cord portions are of the second adjustable subloop.

14. A suture implant protecting kit comprising:
a suture implant comprising one or more suture cords having:
  a stitchable fixation member having a width and length extending between a first end and a second end, wherein the stitchable fixation member is configured to be stitched therethrough to a body;
  an adjustable loop coupled to the first end of the stitchable fixation member by having a first adjustable loop end and second adjustable loop end both extending from the same first end of the stitchable fixation member;
  a fastening member having at least one aperture receiving the adjustable loop through the at least one aperture so that the fastening member is slidable relative to the adjustable loop, and the fastening member is configured for being fastened to a tissue or bone; and
  a stitching loop coupled to the second end of the stitchable fixation member by having a first stitching loop end and second stitching loop end both extending from the same second end of the stitchable fixation member, and the stitching loop is configured to stitch the stitchable fixation member to the body; and
a suture protector retaining at least a portion of the suture implant, the suture protector comprising:
  a tube having a top open end and a bottom open end and lumen therebetween; and
  a cap having a single cap opening and an internal chamber, the cap opening receiving the bottom open end of the tube therethrough;
  wherein a first portion of the suture implant is retained in the internal chamber of the cap, a second portion of the suture implant extends through the lumen of the tube, and a third portion of the suture implant is exposed at the top open end of the tube or extends from the top open end of the tube.

15. The kit of claim 14, wherein:
the first portion of the suture implant includes the fastening member;
the second portion includes at least a portion of the adjustable loop; and
the third portion includes the stitching loop.

16. The kit of claim 15, wherein the stitchable fixation member is at least a portion of the second portion and/or third portion.

17. The kit of claim 15, the suture protector further comprising an elongate divider coupled at one end of the elongate divider to the top open end of the tube, the elongate divider being flexible so as to extend across the top open end of the tube.

* * * * *